(12) United States Patent  
Fisher et al.

(10) Patent No.: US 8,197,513 B2
(45) Date of Patent: Jun. 12, 2012

(54) FACET FIXATION AND FUSION WEDGE AND METHOD OF USE

(75) Inventors: Michael Alan Fisher, Middleborough, MA (US); Richard C. Techiera, North Dartmouth, MA (US); Christopher Mickiewicz, Bridgewater, MA (US); Michael O'Neil, West Barnstable, MA (US)

(73) Assignee: DePuy Spine, Inc., Raynham, MA (US)

(*) Notice: Subject to any disclaimer, the term of this patent is extended or adjusted under 35 U.S.C. 154(b) by 1303 days.

(21) Appl. No.: 11/734,873

(22) Filed: Apr. 13, 2007

(65) Prior Publication Data

US 2008/0255666 A1 Oct. 16, 2008

(51) Int. Cl.
*A61B 17/70* (2006.01)

(52) U.S. Cl. ........................................ 606/247; 606/279
(58) Field of Classification Search .............. 606/60, 606/246, 247, 248, 249, 282, 90
See application file for complete search history.

(56) References Cited

U.S. PATENT DOCUMENTS

| | | | |
|---|---|---|---|
| 3,934,444 A | 1/1976 | Simons |
| 4,011,602 A | 3/1977 | Rybicki et al. |
| 4,263,904 A | 4/1981 | Judet et al. |
| 4,576,534 A | 3/1986 | Barth et al. |
| 4,590,928 A | 5/1986 | Hunt et al. |
| 4,858,603 A | 8/1989 | Clemow et al. |
| 4,878,794 A | 11/1989 | Potucek |
| 4,898,186 A | 2/1990 | Ikada et al. |
| 4,927,421 A | 5/1990 | Goble et al. |
| 4,961,740 A | 10/1990 | Ray et al. |
| 4,988,351 A | 1/1991 | Paulos et al. |
| 5,059,193 A | 10/1991 | Kuslich |
| 5,100,405 A | 3/1992 | McLaren |
| 5,129,904 A | 7/1992 | Illi |
| 5,152,303 A | 10/1992 | Allen |
| 5,156,616 A | 10/1992 | Meadows et al. |
| 5,169,400 A | 12/1992 | Muhling et al. |
| 5,180,388 A | 1/1993 | DiCarlo |
| 5,275,601 A | 1/1994 | Gogolewski et al. |
| 5,314,427 A | 5/1994 | Goble et al. |
| 5,364,400 A | 11/1994 | Rego, Jr. et al. |

(Continued)

FOREIGN PATENT DOCUMENTS

EP 0502698 9/1992

(Continued)

OTHER PUBLICATIONS

International Search Report and Report Opinion dated Sep. 16, 2008 for PCT/US08/59889.

(Continued)

*Primary Examiner* — Eduardo C Robert
*Assistant Examiner* — Jerry Cumberledge
(74) *Attorney, Agent, or Firm* — Nutter McClennen & Fish LLP

(57) ABSTRACT

A spinal implant including an at least one screw disposed within a wedge body is herein provided. The implant can be configured for placement with a facet joint in an intra-facet delivery. Furthermore, the implant can include a fusion-promoting bioactive material thereby providing a single device capable of spinal stabilization and/or fusion. Furthermore, a method of placing such an implant within a facet joint in an intra-facet orientation is hereby provided.

21 Claims, 13 Drawing Sheets

U.S. PATENT DOCUMENTS

| | | | |
|---|---|---|---|
| 5,403,136 A | 4/1995 | Mathys et al. | |
| 5,409,486 A | 4/1995 | Reese | |
| 5,443,509 A | 8/1995 | Boucher et al. | |
| 5,456,685 A | 10/1995 | Huebner | |
| 5,470,334 A | 11/1995 | Ross et al. | |
| 5,487,744 A | 1/1996 | Howland | |
| D368,777 S | 4/1996 | Goble et al. | |
| 5,527,312 A | 6/1996 | Ray | |
| 5,545,163 A | 8/1996 | Miller et al. | |
| 5,558,674 A | 9/1996 | Heggeness et al. | |
| D374,286 S | 10/1996 | Goble et al. | |
| D374,287 S | 10/1996 | Goble et al. | |
| D374,482 S | 10/1996 | Goble et al. | |
| 5,562,672 A | 10/1996 | Huebner et al. | |
| 5,571,104 A | 11/1996 | Li | |
| 5,571,139 A | 11/1996 | Jenkins, Jr. | |
| 5,613,968 A | 3/1997 | Lin | |
| 5,645,547 A | 7/1997 | Coleman | |
| 5,681,311 A | 10/1997 | Foley et al. | |
| 5,697,929 A | 12/1997 | Mellinger | |
| 5,743,912 A | 4/1998 | Lahille et al. | |
| 5,743,914 A | 4/1998 | Skiba | |
| 5,840,078 A | 11/1998 | Yerys | |
| 5,871,486 A | 2/1999 | Huebner et al. | |
| 5,885,300 A | 3/1999 | Tokuhashi et al. | |
| 5,888,228 A * | 3/1999 | Knothe et al. | 623/17.16 |
| 5,925,047 A | 7/1999 | Errico et al. | |
| 5,947,969 A | 9/1999 | Errico et al. | |
| 5,951,560 A | 9/1999 | Simon et al. | |
| 5,964,761 A | 10/1999 | Kambin | |
| 5,968,047 A | 10/1999 | Reed | |
| 5,989,255 A | 11/1999 | Pepper et al. | |
| 6,007,539 A | 12/1999 | Kirsch et al. | |
| 6,030,162 A | 2/2000 | Huebner | |
| 6,045,554 A | 4/2000 | Grooms et al. | |
| 6,048,343 A | 4/2000 | Mathis et al. | |
| 6,080,157 A * | 6/2000 | Cathro et al. | 606/279 |
| 6,096,060 A | 8/2000 | Fitts et al. | |
| 6,099,529 A | 8/2000 | Gertzman et al. | |
| 6,126,663 A | 10/2000 | Hair | |
| 6,162,225 A | 12/2000 | Gertzman et al. | |
| 6,210,442 B1 * | 4/2001 | Wing et al. | 623/17.11 |
| 6,214,007 B1 | 4/2001 | Anderson | |
| 6,214,012 B1 | 4/2001 | Karpman et al. | |
| 6,277,149 B1 | 8/2001 | Boyle et al. | |
| 6,280,443 B1 | 8/2001 | Gu et al. | |
| 6,283,973 B1 | 9/2001 | Hubbard et al. | |
| 6,383,187 B2 | 5/2002 | Tormala et al. | |
| 6,402,757 B1 | 6/2002 | Moore, III et al. | |
| 6,461,373 B2 | 10/2002 | Wyman et al. | |
| 6,464,706 B1 | 10/2002 | Winters | |
| 6,485,518 B1 | 11/2002 | Cornwall et al. | |
| 6,488,683 B2 | 12/2002 | Lieberman | |
| 6,506,192 B1 | 1/2003 | Gertzman et al. | |
| 6,527,773 B1 | 3/2003 | Lin et al. | |
| 6,540,747 B1 | 4/2003 | Marino | |
| 6,565,572 B2 | 5/2003 | Chappius | |
| 6,569,186 B1 | 5/2003 | Winters et al. | |
| 6,575,976 B2 | 6/2003 | Grafton | |
| 6,585,518 B1 | 7/2003 | Jenkins et al. | |
| 6,589,245 B1 | 7/2003 | Weiler et al. | |
| 6,629,977 B1 | 10/2003 | Wolf | |
| 6,641,583 B2 | 11/2003 | Shluzas et al. | |
| 6,648,893 B2 | 11/2003 | Dudasik | |
| 6,666,868 B2 | 12/2003 | Fallin | |
| 6,685,706 B2 | 2/2004 | Padget et al. | |
| 6,723,095 B2 | 4/2004 | Hammerslag | |
| 6,808,526 B1 | 10/2004 | Magerl et al. | |
| 6,811,567 B2 | 11/2004 | Reiley | |
| 6,921,402 B2 | 7/2005 | Contiliano et al. | |
| 6,923,814 B1 | 8/2005 | Hildebrand et al. | |
| 6,945,975 B2 | 9/2005 | Dalton | |
| 6,966,930 B2 * | 11/2005 | Arnin et al. | 623/17.11 |
| 6,976,818 B2 | 12/2005 | Levey et al. | |
| 6,979,333 B2 | 12/2005 | Hammerslag | |
| 6,981,974 B2 | 1/2006 | Berger | |
| 7,056,341 B2 | 6/2006 | Crozet | |
| 7,090,675 B2 | 8/2006 | Songer | |
| 7,101,398 B2 | 9/2006 | Dooris et al. | |
| 7,291,149 B1 | 11/2007 | Michelson | |
| 7,410,789 B2 | 8/2008 | Schlosser et al. | |
| 7,491,221 B2 | 2/2009 | David | |
| 7,699,878 B2 * | 4/2010 | Pavlov et al. | 606/279 |
| 7,708,761 B2 * | 5/2010 | Petersen | 606/247 |
| 7,799,057 B2 * | 9/2010 | Hudgins et al. | 606/247 |
| 7,909,826 B2 | 3/2011 | Serhan et al. | |
| 2001/0029375 A1 | 10/2001 | Betz et al. | |
| 2002/0042615 A1 | 4/2002 | Graf et al. | |
| 2002/0151895 A1 | 10/2002 | Soboleski et al. | |
| 2002/0177898 A1 * | 11/2002 | Crozet | 623/17.11 |
| 2002/0183747 A1 | 12/2002 | Jao et al. | |
| 2003/0032960 A1 | 2/2003 | Dudasik | |
| 2003/0040746 A1 | 2/2003 | Mitchell et al. | |
| 2003/0125740 A1 | 7/2003 | Khanna | |
| 2003/0153921 A1 | 8/2003 | Stewart et al. | |
| 2004/0006342 A1 | 1/2004 | Altarac et al. | |
| 2004/0082956 A1 | 4/2004 | Baldwin et al. | |
| 2004/0087948 A1 | 5/2004 | Suddaby | |
| 2004/0111093 A1 | 6/2004 | Chappuis | |
| 2004/0127906 A1 | 7/2004 | Culbert et al. | |
| 2004/0127989 A1 | 7/2004 | Dooris et al. | |
| 2004/0143267 A1 | 7/2004 | Fallin | |
| 2004/0143268 A1 | 7/2004 | Falahee | |
| 2004/0167520 A1 | 8/2004 | Zucherman et al. | |
| 2004/0186475 A1 | 9/2004 | Falahee | |
| 2004/0225292 A1 | 11/2004 | Sasso et al. | |
| 2004/0225360 A1 | 11/2004 | Malone | |
| 2004/0230192 A1 | 11/2004 | Graf | |
| 2004/0249376 A1 | 12/2004 | Hammerslag | |
| 2004/0254575 A1 | 12/2004 | Obenchain et al. | |
| 2004/0260296 A1 | 12/2004 | Kaiser et al. | |
| 2004/0260298 A1 | 12/2004 | Kaiser et al. | |
| 2005/0015060 A1 | 1/2005 | Sweeney | |
| 2005/0038434 A1 | 2/2005 | Mathews | |
| 2005/0113929 A1 | 5/2005 | Cragg et al. | |
| 2005/0119657 A1 | 6/2005 | Goldsmith | |
| 2005/0124993 A1 | 6/2005 | Chappuis | |
| 2005/0149030 A1 | 7/2005 | Serhan et al. | |
| 2005/0165399 A1 | 7/2005 | Michelson | |
| 2005/0177240 A1 | 8/2005 | Blain | |
| 2005/0192572 A1 | 9/2005 | Abdelgany et al. | |
| 2005/0192580 A1 | 9/2005 | Dalton | |
| 2005/0197660 A1 | 9/2005 | Haid et al. | |
| 2005/0197700 A1 | 9/2005 | Boehm et al. | |
| 2005/0216016 A1 | 9/2005 | Contiliano et al. | |
| 2005/0222681 A1 | 10/2005 | Richley et al. | |
| 2005/0228384 A1 | 10/2005 | Zucherman et al. | |
| 2005/0234459 A1 | 10/2005 | Falahee et al. | |
| 2005/0234551 A1 | 10/2005 | Fallin et al. | |
| 2005/0234552 A1 | 10/2005 | Reiley | |
| 2005/0240188 A1 | 10/2005 | Chow et al. | |
| 2005/0251256 A1 | 11/2005 | Reiley | |
| 2005/0261770 A1 | 11/2005 | Kuiper et al. | |
| 2005/0267480 A1 | 12/2005 | Suddaby | |
| 2005/0273110 A1 | 12/2005 | Boehm et al. | |
| 2006/0004358 A1 | 1/2006 | Serhan et al. | |
| 2006/0004367 A1 | 1/2006 | Alamin et al. | |
| 2006/0004448 A1 | 1/2006 | Casey | |
| 2006/0004449 A1 | 1/2006 | Goble et al. | |
| 2006/0004451 A1 | 1/2006 | Goble et al. | |
| 2006/0009847 A1 | 1/2006 | Reiley | |
| 2006/0009848 A1 | 1/2006 | Reiley | |
| 2006/0015105 A1 | 1/2006 | Warren et al. | |
| 2006/0030948 A1 | 2/2006 | Manrique et al. | |
| 2006/0036243 A1 | 2/2006 | Sasso et al. | |
| 2006/0036323 A1 | 2/2006 | Carl et al. | |
| 2006/0041311 A1 | 2/2006 | McLeer | |
| 2006/0052785 A1 | 3/2006 | Augostino et al. | |
| 2006/0064099 A1 * | 3/2006 | Pavlov et al. | 606/72 |
| 2006/0085068 A1 | 4/2006 | Barry | |
| 2006/0089646 A1 | 4/2006 | Bonutti | |
| 2006/0095036 A1 | 5/2006 | Hammerslag | |
| 2006/0095040 A1 | 5/2006 | Schlienger et al. | |
| 2006/0106381 A1 | 5/2006 | Ferree et al. | |
| 2006/0111179 A1 | 5/2006 | Inamura | |
| 2006/0111779 A1 | 5/2006 | Petersen | |
| 2006/0111782 A1 | 5/2006 | Petersen | |

| | | | |
|---|---|---|---|
| 2006/0122609 A1 | 6/2006 | Mirkovic et al. | |
| 2006/0149239 A1 | 7/2006 | Winslow et al. | |
| 2006/0149254 A1 | 7/2006 | Lauryssen et al. | |
| 2006/0149272 A1 | 7/2006 | Winslow et al. | |
| 2006/0149289 A1 | 7/2006 | Winslow et al. | |
| 2006/0149373 A1 | 7/2006 | Winslow et al. | |
| 2006/0149374 A1 | 7/2006 | Winslow et al. | |
| 2006/0178743 A1 | 8/2006 | Carter | |
| 2006/0190081 A1* | 8/2006 | Kraus et al. | 623/17.11 |
| 2006/0200137 A1 | 9/2006 | Soboleski et al. | |
| 2006/0217714 A1 | 9/2006 | Serhan et al. | |
| 2006/0235388 A1 | 10/2006 | Justis et al. | |
| 2006/0235391 A1 | 10/2006 | Sutterlin | |
| 2006/0241597 A1 | 10/2006 | Mitchell et al. | |
| 2006/0241758 A1 | 10/2006 | Peterman et al. | |
| 2006/0247632 A1 | 11/2006 | Winslow et al. | |
| 2006/0247633 A1 | 11/2006 | Winslow et al. | |
| 2006/0247650 A1 | 11/2006 | Yerby et al. | |
| 2006/0264953 A1 | 11/2006 | Falahee | |
| 2006/0271054 A1 | 11/2006 | Sucec et al. | |
| 2006/0276790 A1 | 12/2006 | Dawson et al. | |
| 2006/0276801 A1 | 12/2006 | Yerby et al. | |
| 2006/0293658 A1 | 12/2006 | Sharim | |
| 2007/0016191 A1 | 1/2007 | Culbert et al. | |
| 2007/0016195 A1 | 1/2007 | Winslow et al. | |
| 2007/0016196 A1 | 1/2007 | Winslow et al. | |
| 2007/0016218 A1 | 1/2007 | Winslow et al. | |
| 2007/0055236 A1 | 3/2007 | Hudgins et al. | |
| 2007/0055373 A1 | 3/2007 | Hudgins et al. | |
| 2007/0073290 A1 | 3/2007 | Boehm | |
| 2007/0118132 A1 | 5/2007 | Culbert et al. | |
| 2007/0135814 A1 | 6/2007 | Farris | |
| 2007/0233093 A1 | 10/2007 | Falahee | |
| 2007/0250166 A1 | 10/2007 | McKay | |
| 2008/0103512 A1 | 5/2008 | Gately | |
| 2008/0177334 A1 | 7/2008 | Stinnette | |
| 2008/0234758 A1 | 9/2008 | Fisher et al. | |
| 2008/0255618 A1 | 10/2008 | Fisher et al. | |
| 2008/0255622 A1 | 10/2008 | Mickiewicz et al. | |
| 2008/0275507 A1 | 11/2008 | Triplett et al. | |
| 2008/0306537 A1 | 12/2008 | Culbert | |
| 2008/0306555 A1 | 12/2008 | Patterson et al. | |
| 2008/0319483 A1 | 12/2008 | Triplett et al. | |
| 2008/0319484 A1 | 12/2008 | Fauth | |
| 2008/0319485 A1 | 12/2008 | Fauth et al. | |
| 2008/0319488 A1 | 12/2008 | Helgerson | |
| 2008/0319489 A1 | 12/2008 | Triplett | |
| 2009/0012566 A1 | 1/2009 | Fauth | |
| 2009/0036926 A1 | 2/2009 | Hestad | |
| 2009/0036986 A1 | 2/2009 | Lancial et al. | |
| 2009/0099602 A1 | 4/2009 | Aflatoon | |
| 2009/0105716 A1 | 4/2009 | Barrus | |
| 2009/0125066 A1* | 5/2009 | Kraus et al. | 606/279 |
| 2009/0138053 A1 | 5/2009 | Assell et al. | |
| 2009/0192551 A1 | 7/2009 | Cianfrani et al. | |
| 2009/0312763 A1 | 12/2009 | McCormack et al. | |

FOREIGN PATENT DOCUMENTS

| | | | |
|---|---|---|---|
| EP | 0856293 A1 | 8/1998 | |
| EP | 1210914 A1 | 6/2002 | |
| EP | 1248568 A2 | 10/2002 | |
| EP | 1452146 A1 | 9/2004 | |
| EP | 1585449 A1 | 10/2005 | |
| EP | 1813216 A1 | 8/2007 | |
| WO | WO-0041636 A1 | 7/2000 | |
| WO | 0062684 A1 | 10/2000 | |
| WO | 0141681 A1 | 6/2001 | |
| WO | WO-0141681 A1 | 6/2001 | |
| WO | 0234120 A2 | 5/2002 | |
| WO | 03007829 A1 | 1/2003 | |
| WO | 2004043278 A1 | 5/2004 | |
| WO | 2004100808 A1 | 11/2004 | |
| WO | 2004110288 A2 | 12/2004 | |
| WO | 2005004733 A1 | 1/2005 | |
| WO | 2005042036 A2 | 5/2005 | |
| WO | 2005060845 A1 | 7/2005 | |
| WO | 2005076974 A2 | 8/2005 | |
| WO | 2005097005 A1 | 10/2005 | |
| WO | 2006007739 A1 | 1/2006 | |
| WO | 2006009855 A2 | 1/2006 | |
| WO | WO-2006002684 A1 | 1/2006 | |
| WO | 2006047707 A2 | 5/2006 | |
| WO | 2006057943 A2 | 6/2006 | |
| WO | 2006065774 A1 | 6/2006 | |
| WO | 2006086241 A2 | 8/2006 | |
| WO | 2006096803 A2 | 9/2006 | |
| WO | 2006116119 A2 | 11/2006 | |
| WO | 2007019710 A1 | 2/2007 | |
| WO | 2007041698 A1 | 4/2007 | |
| WO | 2007047711 A2 | 4/2007 | |
| WO | 2007063399 A1 | 6/2007 | |
| WO | 2007075454 A1 | 7/2007 | |
| WO | 2007120903 A2 | 10/2007 | |
| WO | 2007127610 A1 | 11/2007 | |
| WO | 2008124196 A2 | 10/2008 | |
| WO | WO-2008153732 A1 | 12/2008 | |
| WO | 2009018220 A1 | 2/2009 | |
| WO | 2009067486 A2 | 5/2009 | |
| WO | WO-2009138053 A1 | 11/2009 | |

OTHER PUBLICATIONS

International Search Report and Written Opinion dated Jul. 25, 2008 for PCT/US08/50194.

International Search Report and Written Opinion dated Sep. 24, 2008 for PCT/US08/59866.

Frank M. Phillips, M.D., "Effect of Supplemental Translaminar Facet Screw Fixation on the Stability of Stand-Alone Anterior Lumbar Interbody Fusion Cages Under Physiologic Compressive Preloads", Spine vol. 29, No. 16, pp. 1731-1736, , Lippincott Williams & Wilkins, Inc © 2004, Augus.

Youssef Masharawi, PhD, et al., "Facet Orientation in the Thoracolumbar Spine", Spine vol. 29, No. 16, pp. 1755-1763, © 2004, Lippincott Williams & Wilkins, Inc.

Brian P. Beaubien, BME, et al., "Posterior Augmentation of an Anterior Lumbar Interbody Fusion", Spine vol. 29, No. 19, pp. E406-E412, © 2004, Lippincott Williams & Wilkins, Inc.

Frank Kandziora, M.D., et al., "Biomechanical Testing of the Lumbar Facet Interference Screw", Spine vol. 30, No. 2, pp. E34-E39, © 2005, Lippincott Williams & Wilkins, Inc.

Neil Duggal, M.D., et al., "Unilateral Cervical Facet Dislocation: Biomechanics of Fixation", Spine vol. 30, No. 7, pp. E164-E168, © 2005, Lippincott Williams & Wilkins, Inc.

Youssef masharawi, PhD, BPT, et al., "Facet Tropism and Interfacet Shape in the Thoracolumbar Vertebrae", Spine vol. 30, No. 11, pp. E281-E292, © 2005, Lippincott Williams & Wilkins, Inc., Aug. 15, 2004.

Brian P. Beaubien, BME, et al., "In Vitro, Biomechanical Comparison of an Anterior Lumbar Interdody Fusion with an Anteriorly Placed, Low-Profile Lumbar Plate and Posteriorly Placed Pedicle Screws or Translaminar Screws", Spine vol. 30, No. 16, pp. 1846-1851, © 2005, Lippincott Williams & Wilkins, Inc.

David W. Polly, Jr., M.D., et al. "Surgical Treatment for the Painful Motion Segment", Spine vol. 30, No. 16S, pp. S44-S51, © 2005, Lippincott Williams & Wilkins, Inc.

Douglas Burton, M.D., et al., "Biomechanical Analysis of Posterior Fixation Techniques in a 360° Arthrodesis Model", Spine vol. 30, No. 24, pp. 2765-2771, © 2005, Lippincott Williams & Wilkins, Inc.

Langston T, Holly, M.D., et al., "Percutaneous Placement of Posterior Cervical Screws Using Three-Dimensional Fluoroscopy", Spine vol. 31, No. 5, pp. 536-540, © 2006, Lippincott Williams & Wilkins, Inc.

Frank M. Phillips, M.D., et al., "Radiographic Criteria for Placement of Translaminar Facet Screws", The Spine Journal 4 (2004) 465-467.

Andrew V. Slucky, M.D., et al., "Less Invasive Posterior Fixation Method Following Transforaminal Lumbar Interbody Fusion: a Biomechanical Analysis", The Spine Journal 6 (2006) 78-85.

U.S. Appl. No. 12/834,397 for "Pedicular Facet Fusion Screw With Plate" filed Jul. 12, 2010.

U.S. Appl. No. 12/834,417 for " Pedicular Facet Fusion Screw With Plate" filed Jul. 12, 2010.

Brain W. Su, MD, et al. "An Anatomic and Radiographic Study of Lumbar Facets Relevant to Percutaneous Transfacet Fixation", Spine vol. 34, No. 11, pp. E384-E390, 2009, Lippincott Williams & Wilkins.

Ch. D. Ray, "Transfacet Decompression with Dowel Fixation: a New Technique for Lumbar Lateral Spinal Stenosis", Acta Neurochirurgica, Suppl. 43, 48-54 (1988) © by Springer-Verlag 1988.

Th.-M. Markwalder, et al, "Translaminar Screw Fixation in Lumbar Spine Pathology", Acta Neurochir (Wien) (1989) 99: 58-60.

Matthijs R. Krijnen, M.D., et al, "Does Bioresorbable Cage Material Influence Segment Stability in Spinal Interbody Fusion?" Clinical Orthopaedics and Related Research, No. 448, pp. 33-38 © 206 Lippincott Williams & Wilkins.

D.A. McQueen, M.D. et al., "Knee Arthrodesis with the Wichita Fusion Nail", Clinical Orthopaedics and Related Research, No. 446, pp. 132-139, © 2006 Lippincott Williams & Wilkins.

D.Grob et al., Translaminar screw fixation in the lumbar spine: technique, indications, results, Eur Spine J (1998) vol. 7:178-186, © Springer-Verlag 1998.

Hans Trouillier, et al., "A Prospective Morphological Study of Facet Joint Integrity Following Intervertebral Disc Replacement with the CHARITE™ Artificial Disc", Eur Spine J. (2006) vol. 15: 174-182 DOI 10.1007/s00586-005-1010-7, Jul. 2005.

Thomas Tischer, et al., "Detailed Pathological Changes of Human Lumbar Facet joints L1-L5 in Elderly Individuals", Eur Spine J Mar. 2006;15(3):308-15, Epub July, vol. 15, 2005.

Nicola C. Gries, et al., "Early Histologic Changer in Lower Lumbar Discs and Facet joints and their Correlation", Eur Spine J (2000) 9:23-29 © Springer-Verlag 2000, Feb. 2000.

Anil Sethi, et al., "Transforaminal Lumbar Interbody Fusion Using Unilateral Pedicle Screws and a Translaminar Screw", Eur Spine J (2009) 18:430-434 DOI 10.1007/s00586-008-0825-4, Mar. 2009.

Sung-Min Kim, M.D., et al., "A Biomechanical Comparison of Supplementary Posterior Translaminar Facet and Transfacetopedicular Screw Fixation after Anterior Lumbar Interbody Fusiion", J Neurosurg (Spine 1) 1:101-107, Jul. 2004.

Jee-Soo Jang, M.D., et. al., "Clinical Analysis of Percutaneous Facet Screw Fixation after Anterior Lumbar Interbody Fusion", J Neurosurg: Spine 3:40-46, Jul. 2005.

Jee-Soo Jang, M.D., et. al., "Minimally Invasive Transforaminal Lumbar Interbody Fusion with Ipsilateral Pedicle Screw and Contralateral Facet Screw Fixation", J Neurosurg: Spine 3:218-223, Sep. 2005.

Natalie M. Best, et al., "Efficacy of Translaminar Facet Screw Fixation in Circumferential Interbody Fusions As Compared to Pedicle Screw Fixation", J Spinal Disord Tech, vol. 19, No. 2, Apr. 2006.

John W. Klekamp, et. al., "Cervical Transfacet Versus Lateral Mass Screws: A Biomechanical Comparison", Journal of Spinal Disorders, vol. 13, No. 6, pp. 515-518, 2000, Lippincott Williams & Wilkins, Inc., Philadelphia: Dec. 2000.

Harri Pihajamäki, et al., "Tissue Response to Polyglycolide, Polydioxanone, Polylevolactide, and Metallic Pins in Cancellous Bone: An Experimental Study on Rabbits", Journal of Orthopaedic Research, Aug. 2006.

Youn-Kwan Park, M.D., "Facet Fusion in the Lumbosacral Spine: A 2-year Follow-Up Study", vol. 51, No. 1, Jul. 2002.

Albert C. Schmidt, M.D., et al., "Lumbar Fusion Using Facet Inlay Grafts*", Southern Medical Journal, vol. 68, No. 2., Feb. 1975.

Philipp Schleicher, M.D., et al., "Biomechanical Evaluation of Different Asymmetrical Posterior Stabilization Methods for Minimally Invasive Transforaminal Lumbar Interbody Fusion", J. Neurosurg: Spine, vol. 9, Oct. 2008.

Yasuaki Tokuhashi, M.D., et al., "C1-C2 Intra-articular Screw Fixation for Atlantoaxial Posterior Stabilization", Spine vol. 25, No. 3, pp. 337-241, Lippincott Williams & Wilkins, Inc., Feb. 1, 2000.

Lisa A. Ferrara, et al., "A Biomechanical Comparison of Facet Screw Fixation and Pedicle Screw Fixation", Spine vol. 28, No. 12, pp. 1226-1234, Lippincott Williams & Wilkins, Jun. 15, 2003.

Yukihiro Kai, M.D., et al., "Posterior Lumbar Interbody Fusion Using Local Facet Joint Autograft and Pedicle Screw Fixation", Spine vol. 29, No. 1, pp. 41-46, Lippincott Williams & Wilkins, Inc., Jan. 1, 2004.

Frank M. Phillips, M.D., "Effect of Supplemental Translaminar Facet Screw Fixation on the Stability of Stand-Alone Anterior Lumbar Interbody Fusion Cages Under Physiologic Compressive Preloads", Spine vol. 29, No. 16, pp. 1731-1736, Lippincott Williams & Wilkins, Inc., Aug. 2004.

Akira Igarashi, M.D., et al., "Inflammatory Cytokines Released from the Facet Joint Tissue in Degenerative Lumbar Spinal Disorders", Spine vol. 29, No. 19, pp. 2091-2095, Lippincott Williams & Wilkins, Inc., Oct. 1, 2004.

Extended European Search Report issued Nov. 7, 2011 for Application No. 08745489.8 (4 pages).

International Search Report and Written Opinion mailed Nov. 9, 2011 for Application No. PCT/US2011/042335 (16 pages).

* cited by examiner

FACET FIXATION AND FUSION WEDGE AND METHOD OF USE

FIELD OF THE INVENTION

The present invention relates to methods and devices for spinal stabilization and fusion, and particularly to stabilization and fusion of a facet joint.

BACKGROUND OF THE INVENTION

The vertebrae in a patient's spinal column are linked to one another by the intevertebral disc and the facet joints. This three joint complex controls the movement of the vertebrae relative to one another. Each vertebra has a pair of articulating surfaces located on the left side, and a pair of articulating surfaces located on the right side, and each pair includes a superior articular surface and an inferior articular surface. Together the superior and inferior articular surfaces of adjacent vertebra form a facet joint. Facet joints are synovial joints, which means that each joint is surrounded by a capsule of connective tissue and produces a fluid to nourish and lubricate the joint. The joint surfaces are coated with cartilage allowing the joints to move or articulate relative to one another.

Diseased, degenerated, impaired, or otherwise painful facet joints and/or discs can require surgery to restore function to the three joint complex. In the lumbar spine, for example, one form of treatment to stabilize the spine and to relieve pain involves the fusion of the facet joint.

One known technique for stabilizing and treating the facet joint involves a trans-facet fusion in which pins, screws or bolts penetrate the lamina to fuse the joint. Such a technique has associated with it the risk of further injury to the patient as such translamina facet instrumentation can be difficult to place in such a way that it does not violate the spinal canal and/or contact the dura of the spinal cord or the nerve root ganglia. Further, trans-facet instrumentation has been known to create a rotational distortion, lateral offset, hyper-lordosis, and/or intervertebral foraminal stenosis at the level of instrumentation.

Examples of facet instrumentation currently used to stabilize the lumbar spine include trans-lamina facet screws ("TLFS") and trans-facet pedicle screws ("TFPS"). TLFS and TFPS implants provide reasonable mechanical stability, but, as noted above, they can be difficult to place, have long trajectories, and surgical access can be confounded by local anatomy. In some instances these implants can result in some degree of foraminal stenosis.

Accordingly, there is a need for instrumentation and techniques that facilitate the safe and effective stabilization of facet joints.

SUMMARY OF THE INVENTION

Spinal implants and methods relating to stabilization and/or fusion of a facet joint via intra-facet delivery of the implants are provided. In general, the implant functions as a sort of mechanical key that prevents sliding motion between the diarthroidal surfaces of the facet joint. Further, the spinal implant can include a fusion-promoting bioactive material thereby allowing for a single spinal implant capable of providing both fixation and fusion of a desired facet joint. Various aspects of the implants and method are summarized immediately below.

In one aspect, a method is provided for facet joint stabilization which includes surgically delivering a spinal implant to a facet joint in an intra-facet configuration. The spinal implant includes a wedge body having a distal, leading end, a proximal, trailing end, and opposed bone-facing surfaces running there between. The height of the wedge body can remain substantially constant from the distal to proximal end, can increase (continuously or variably) from the distal to proximal end, or the wedge body can include a tapered leading edge of any desired length. The wedge body further includes an opening formed in each of the bone contacting surfaces such that each opening communicates with a cavity formed in at least a portion of an interior of the wedge body.

Next, at least one drive screw can be disposed within the cavity of the wedge body such that a threaded portion of the screw(s) protrudes from each opening of the opposed bone-contacting surfaces. The screw can be positioned such that a longitudinal axis of the screw is substantially collinear with a longitudinal axis of the wedge body. Furthermore, two screws can be disposed within the wedge body such that each screw is mounted on opposite sides of a longitudinal axis of the wedge body. Next, a screw head can extend from a proximal end of the screw such that the screw head is positioned adjacent the trailing edge of the wedge body so as to be surgically accessible. The screw head can allow for a user to exert a rotational force on the screw.

The screw can be configured relative to the wedge body in various manners. For example, the screw can have a major diameter and a minor diameter such that the major diameter is greater than a maximum height of the wedge body thereby allowing the threads to protrude from the openings of the opposed bone-contacting surfaces, while the minor diameter of the screw can be less than or equal to the minimum height of the wedge body. In alternative embodiments, the minor diameter can be greater than the height of the wedge body.

The threads extending from each opening can be configured to serve various purposes. For example, the threads can be configured to engage opposite inferior and superior surfaces of a facet joint, and subsequently advance the wedge body between such faces of the facet joint in an intra-facet orientation. Further, the threads can also be configured to allow for a desired distraction of the facet joint as the implant resides within the facet joint.

The wedge body can be formed of or include (e.g., a coating) various materials. For example, the wedge body can include a fusion-promoting bioactive material. The bioactive material can be any material capable of actively participating in spinal fusion. For example, the bioactive fusion-promoting material can include allograft bone, tricalcium phosphate (TCP), hydroxyapatite, biocoral hydroxyapatite, bioglass, and polymer composites. Additionally, the wedge body can include a wide range of non-bioactive materials (e.g., titanium, titanium alloys, ceramics, polymers).

The opposed bone contacting surfaces of the wedge body can include various features which facilitate and/or enhance spinal stabilization and/or fusion. For example, at least one of the opposed bone-facing surfaces can be textured to help prevent sliding of the wedge relative to the opposed faces of the facet joint. Next, at least one of the bone-contacting surfaces can include protrusions (e.g., barbs) capable of enhancing placement of the implant within the facet joint by increasing a friction between the bone-facing surface and the corresponding facet face. Additionally, the bone-contacting surface can be porous thereby allowing for bone in-growth into and/or through the wedge body thereby allowing the wedge body to be further solidified within the facet joint.

The method can further include engaging the thread to opposing faces of the facet joint, and rotating the thread to advance the wedge body into the facet joint.

In another aspect, the method can include surgically delivering at least one intra-facet wedge to a facet joint in an intra-facet configuration. Similar to above, a screw can be disposed within the wedge body such that a threaded portion of the screw protrudes from the opposed bone-contacting surfaces of the wedge body. Next, the method can include engaging the threads to opposing faces of the facet joint, and rotating the thread to advance the wedge body into the facet joint. The method can further include adding a fusion-promoting bioactive material to the wedge body thereby allowing for a single spinal implant capable of spinal fixation and fusion. As an added advantage, the method can allow for the spinal implant to be delivered in a minimally invasive procedure.

In another aspect, a spinal implant is provided which includes a wedge body formed around at least one drive screw such that a threaded portion of the drive screw protrudes from opposed bone contacting surfaces of the wedge body. The wedge body can be configured for placement within the facet joint in an intrafacet configuration. In this aspect, a portion of the screw can be configured to protrude from the trailing end of the wedge body.

These and other aspects of the presently disclosed devices and methods are discussed in detail below.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

In general, the spinal implants disclosed herein are configured for intra-facet placement within a facet joint. That is, the implants are configured to be placed in the plane of the facet joint, between the diarthroidal surfaces of the facet joint and as a mechanical spacer to distract the facet faces and relieve forminal stenosis. As such, the implants function in the manner of a mechanical key that prevents sliding motion between the diarthroidal joint surfaces. The implants disclosed herein also stabilize the joint by distracting the facet faces and placing the joint capsule in tension. Such distraction of the facet face is believed to contribute to alleviating intervertebral foraminal stenosis. Components of the implant can be adapted in various manners (e.g., selection of material, dimensions, surface features, etc.) so as to provide an implant capable of adapting to various facet joint configurations. Additionally, various components of the implant can include a fusion-promoting bioactive material capable of actively participating in joint fusion. As such, the presently disclosed embodiments provide a versatile, single spinal implant capable of providing both spinal fixation and fusion of a facet joint via intra-facet placement of the implant within a facet joint.

Figure 1A:
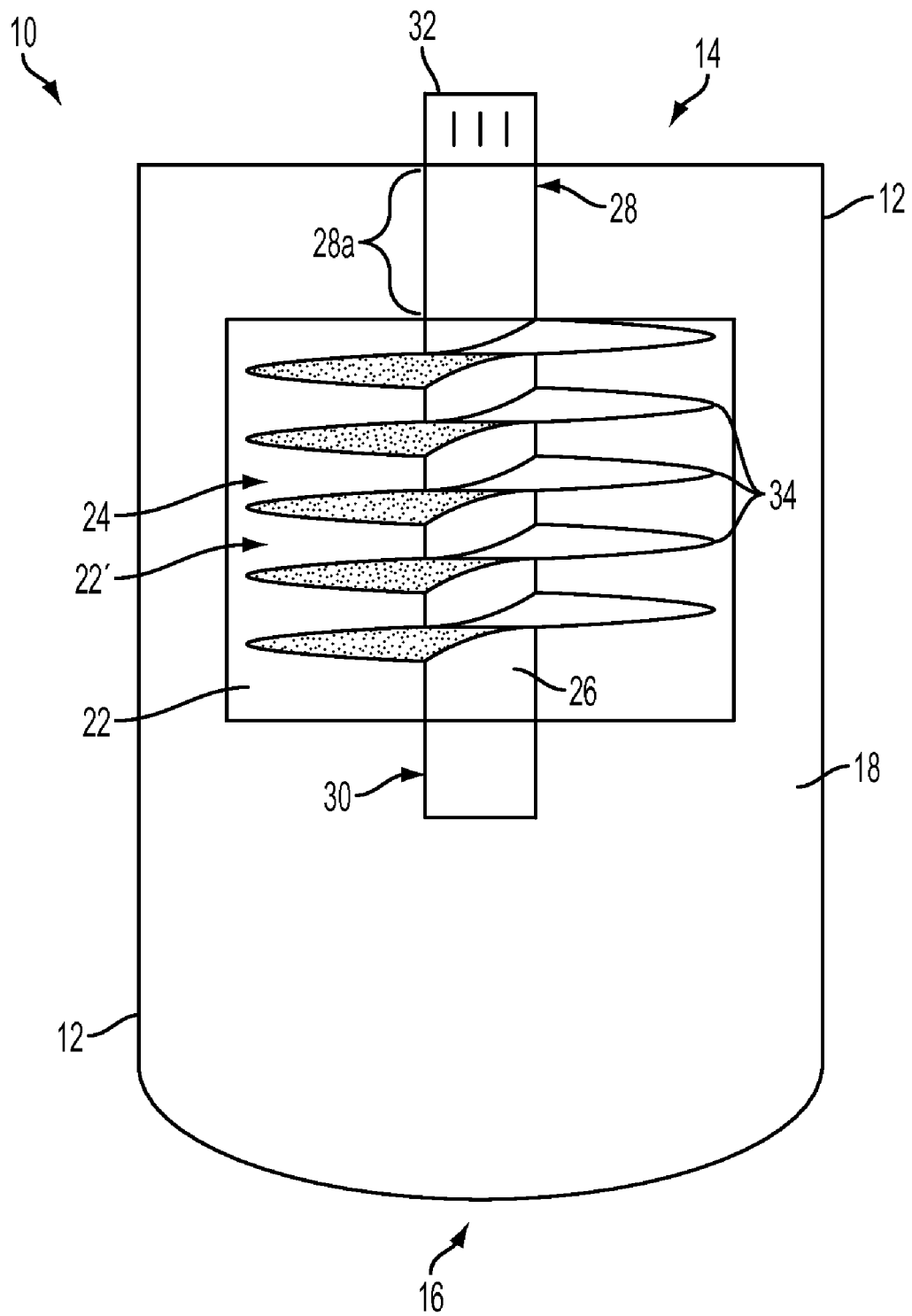
FIG. 1A is a top view of an exemplary embodiment of a spinal implant according to one aspect of the invention.
Figure 2:
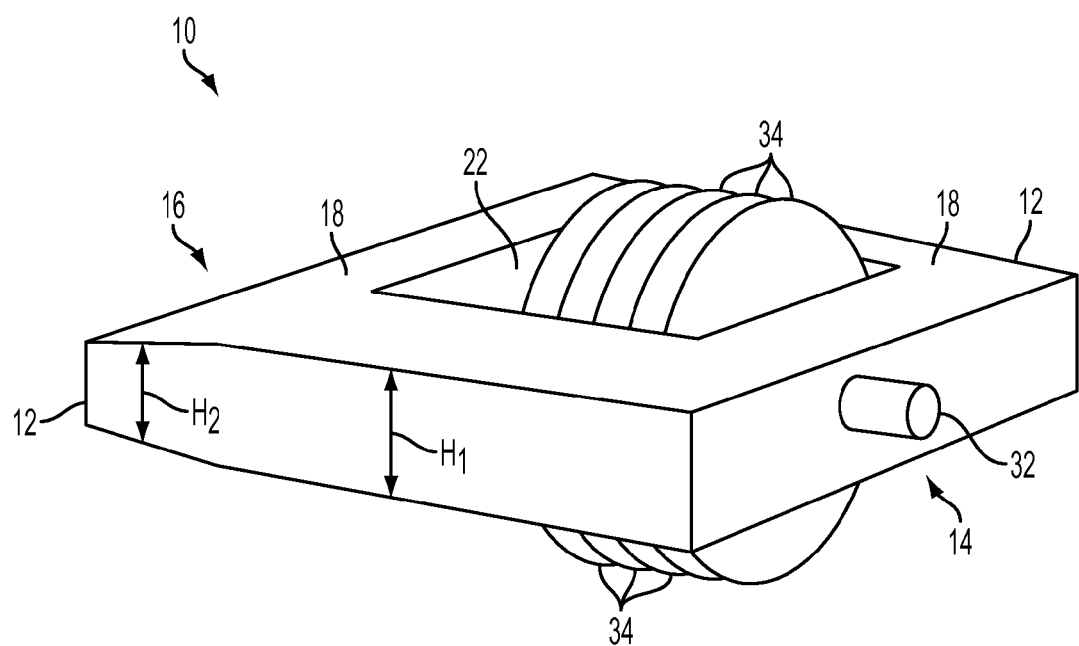
FIG. 2 is a perspective view of the spinal implant of FIG. 1A.

FIG. 1A illustrates an exemplary embodiment of a spinal implant 10 that includes a wedge body 12 having a distal, leading end 16, opposed bone contacting surfaces 18, 20 (bottom facing surface 20 shown in FIGS. 2, 3A, 3B), and a proximal, trailing end 14. The wedge body 12 further includes an opening 22 formed in the top bone contacting surface 18, and a corresponding opening 22' in the bottom bone facing surface 20. As will be shown, each opening 22, 22' communicates with a cavity formed in at least a portion of an interior of the wedge body 12. At least one screw 24 can be disposed within the cavity of the wedge body 12 such that threads 34 formed on at least a portion of the screw 24 protrude from each of the openings 22, 22' beyond the bone contacting surfaces 18, 20. The threads 34 can be configured to advance the wedge body between opposed inferior and superior surfaces of a facet joint when implanted in an intra-facet configuration. Additionally, the threads can be configured to distract opposing faces of the facet joint in order to provide additional joint stabilization.

Figure 1B:
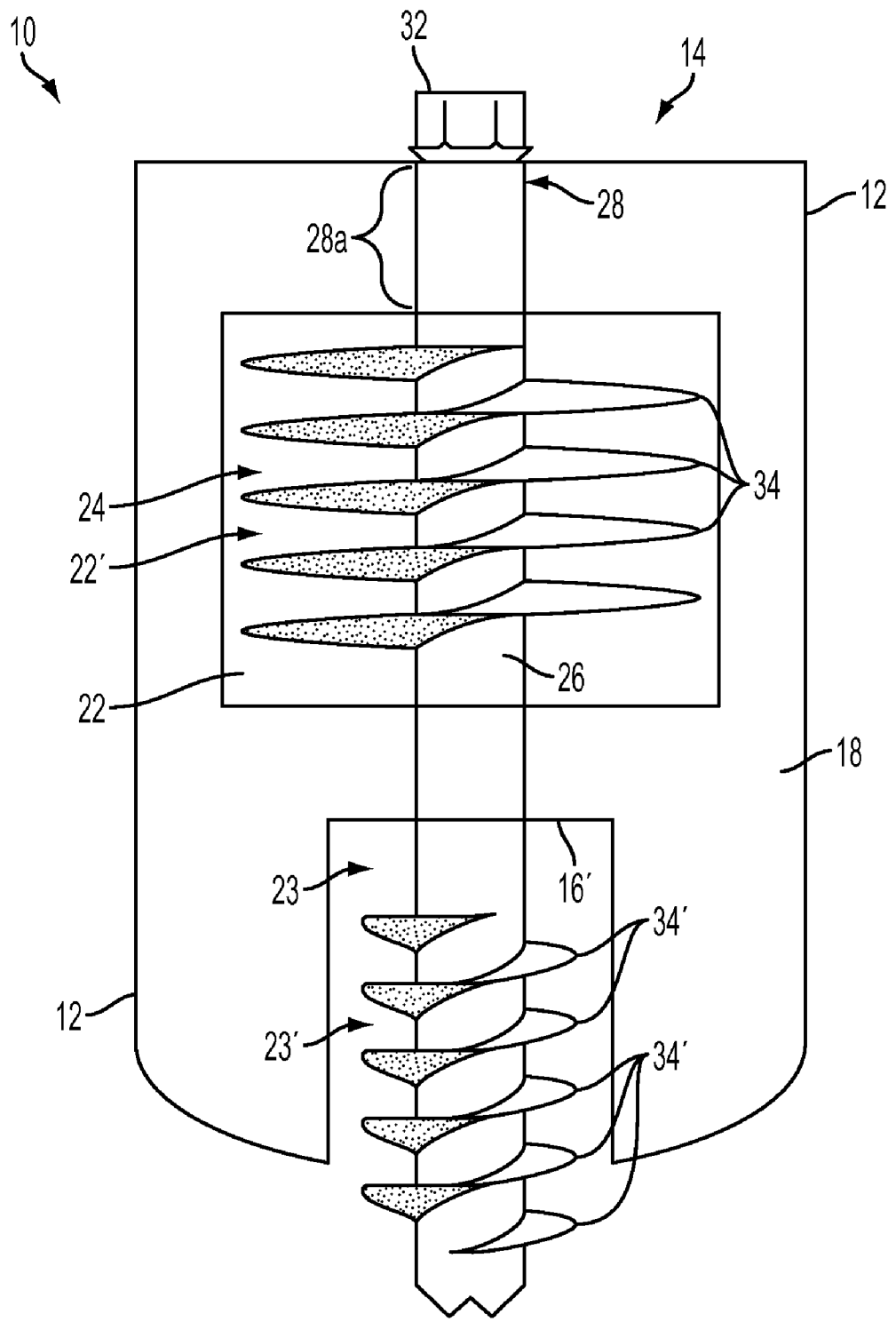
FIG. 1B is a top view of an alternative embodiment of a spinal implant.

FIG. 1B provides an alternative embodiment wherein each bone-contacting surface 18, 20 includes a second opening 23, 23' thereby allowing the screw 24 to extend beyond the distal end 16' of the wedge body 12. In such an embodiment, a second thread 34' can be configured on the distal section of the screw 24. As will be discussed in detail below, either or both of the threads 34, 34' can be configured to facilitate placement within the facet joint and/or configured to participate in distraction of the facet joint. These and other features are discussed in detail below.

In general, the wedge body 12 can take any shape that allows for intra-facet placement of the implant 10 within a facet joint. For example, the wedge body 12 can be substantially oval shaped, rectangular, square, circular, etc. In the exemplary embodiment, shown in FIGS. 1A and 2, the wedge body 12 includes a distal, leading end 16, and a trailing, proximal end 14. Further, the wedge body 12 includes opposed bone-contacting surfaces 18, 20 extending between the distal 16 and proximal 14 ends. More specifically, the wedge body 12 includes a top bone-contacting surface 18, and a bottom bone-contacting surface 20. As will be discussed below, the opposed surfaces 18, 20 can include various features and/or materials that facilitate fixation of the implant with the joint and/or fusion of the desired facet joint.

Figure 3A:
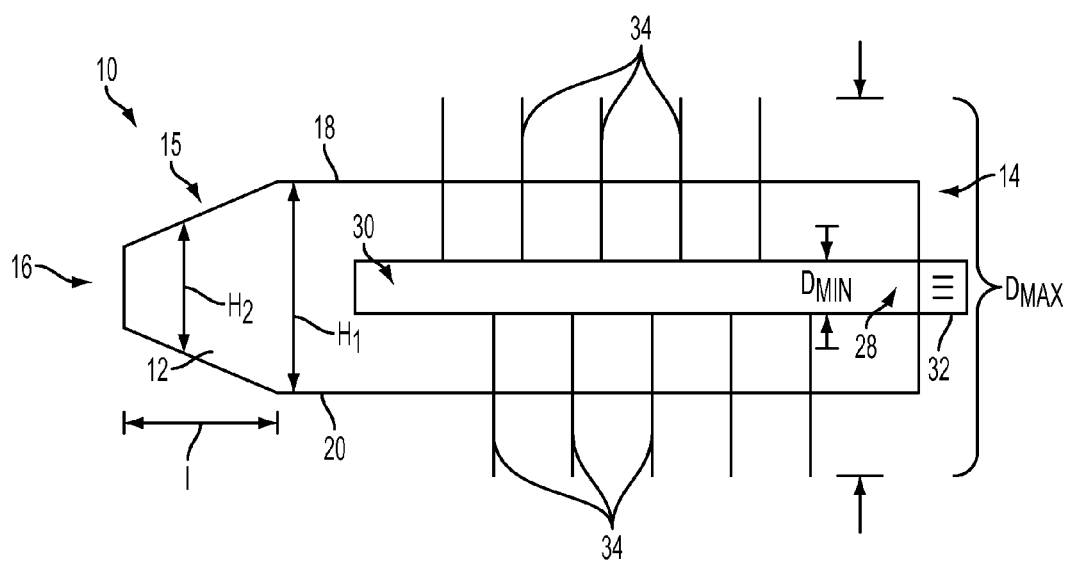
FIG. 3A is a side-view of the spinal implant of FIG. 1A.
Figure 3B:
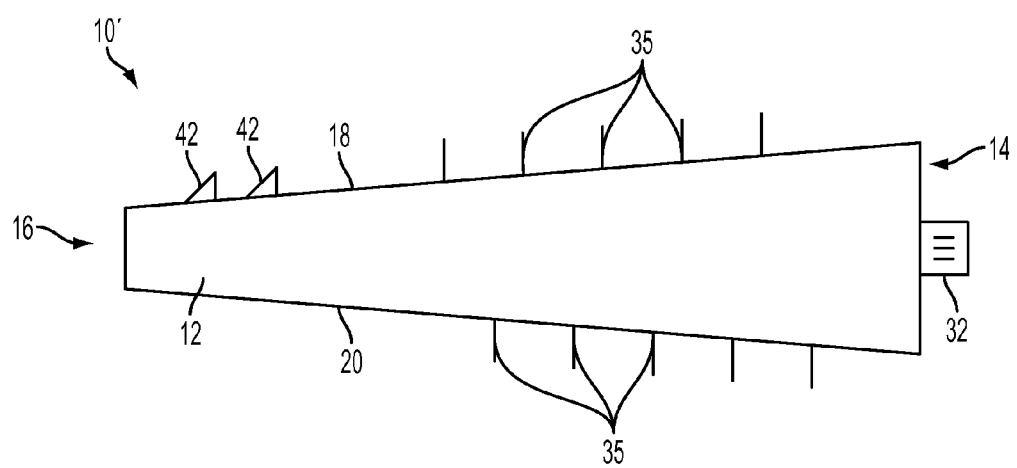
FIG. 3B is a side-view of an alternative embodiment of a spinal implant.

The wedge body 12 can include a height defined by the vertical distance between the opposed surfaces 18, 20. In general, the height of the wedge body can be any height capable of allowing for the desired intra-facet placement of the implant 10 with the facet joint. For example, the height of the wedge body 12 can be substantially constant from the distal 16 to proximal 14 end of the wedge body 12. Alternatively, the height of the wedge body 12 can vary from the distal 16 to proximal 14 ends of the wedge body 10. Furthermore, the wedge body 10 can include a tapered leading edge 15 that extends over any desired distance from the distal end 16. FIG. 3A is a side view of an example of the implant 10 of FIGS. 1A and 2 wherein the distal end 16 of the wedge body 12 includes such a tapered leading edge. As shown, the tapered leading edge 15 includes a length (1) representing the distance of increasing height (for example, $H_2$) over which the tapered leading edge extends until it reaches a desired, maximum height ($H_1$). One skilled in the art will appreciate that a variety of other tapered designs are possible as well. For example, FIG. 3B is an alternative embodiment of the implant 10' in which the height of the wedge body 12 continuously or variably increase from the distal 16 to the proximal end 14. As will appreciated by those of skill in the art, any such height or height profile from the distal 16 to proximal end 14 of the wedge body 12 is within the spirit and scope of the present invention.

As stated above, the width, length, and height of the wedge body can be adapted for intra-facet placement within the facet joint. In an exemplary embodiment, the width of the wedge body 12 can range from about 5 mm to about 30 mm, while the height of the wedge body 12 can range from about 1 mm to about 20 mm. Also, the length of the wedge body 12 can range from about 3 mm to about 30 mm. As stated above, the height and/or width of the wedge body 12 can vary along the length of the wedge body.

Referring back to FIGS. 1A, 1B, and 2, the opposed bone-contacting faces 18, 20 can each include an opening 22, 22' in communication with a central cavity. Generally, the shape and size of the top opening 22 and the bottom opening 22' correspond to one another so as to provide a passageway through the wedge body 12 via the inner cavity. Further, the shape and size of each opening 22, 22' can include any desired shape such as substantially oval, rectangular, square, circular, etc. As will be discussed in detail below, in an exemplary embodiment, the openings 22, 22' and cavity are configured to receive a drive screw 24 such that threads 34 of the screw 24 protrude from each opening 22, 22' beyond the bone-contacting faces 18, 20. The various features of the screw 24 and engagement of the screw 24 to the wedge body 12 will be discussed in detail below.

Looking at the embodiment of FIG. 1B, the opposed bone-contacting faces 18, 20 can each also include a second opening 23, 23' wherein the second openings 23, 23' allow for a distal portion of the screw having a second thread 34' to extend beyond the distal edge 16' of the wedge body 12. Generally, the shape and size of the top opening 23 and the bottom opening 23' correspond to one another. Further, the shape and size of each opening 23, 23' can include any desired shape such as substantially semi-circular, U-shaped, etc. As will be discussed in detail below, in an exemplary embodiment, the openings 23, 23' are configured such that thread 34' can protrude from each opening 23, 23' beyond the bone-contacting faces 18, 20. The various features of the screw 24 and engagement of the screw 24 to the wedge body 12 will be discussed in detail below.

Figure 4:
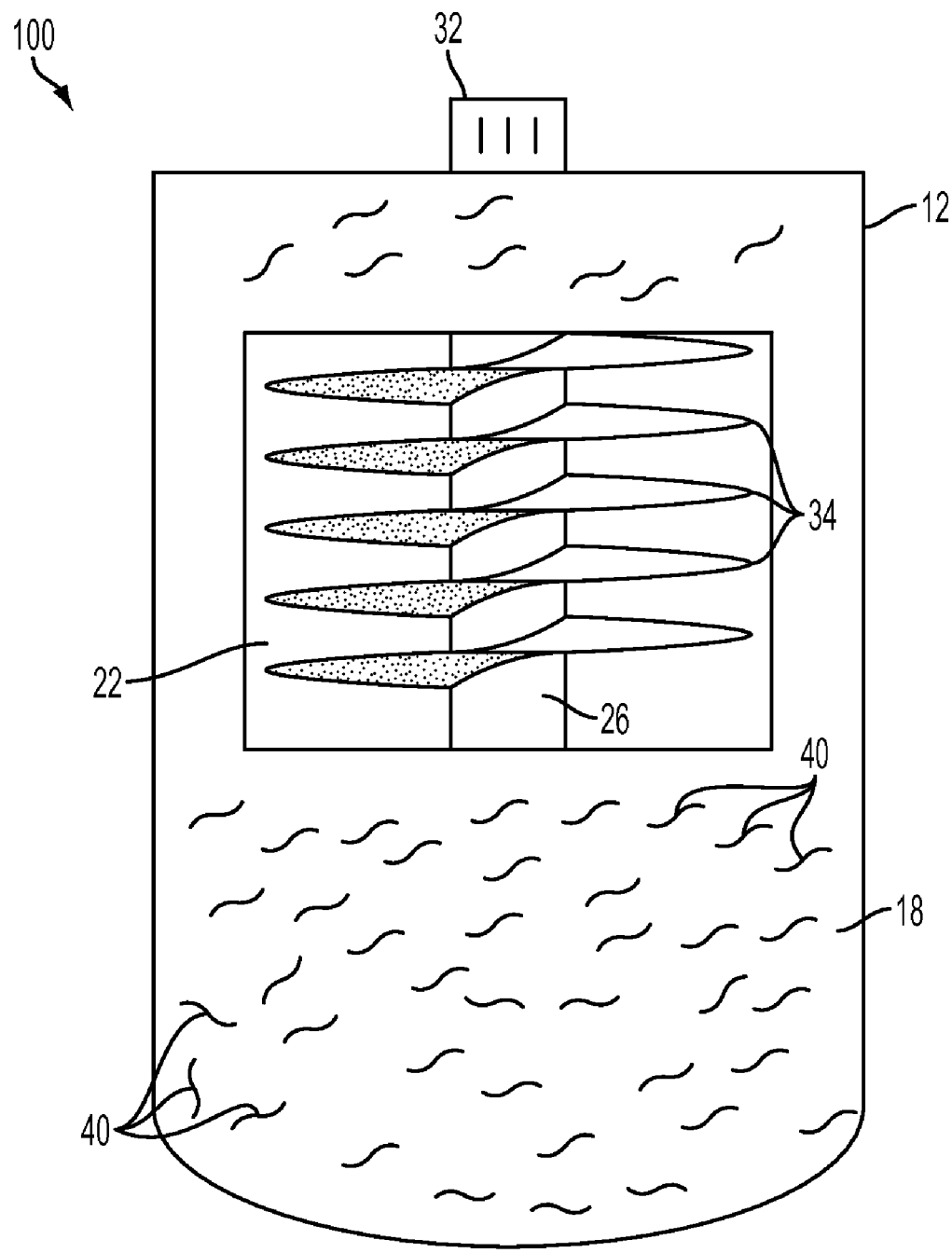
FIG. 4 is a top view of a further embodiment of a spinal implant according to the present invention.

In one embodiment, the opposed bone facing surfaces 18, 20 can be substantially smooth and linear. However, in other embodiments, surfaces 18, 20 can be adapted to enhance spinal stabilization and/or fusion. For example, FIG. 4 shows an embodiment of the implant 100 wherein at least a portion of the top bone-contacting surface 18 includes a surface texture 40 that allows for increased friction between the bone-contacting surface 18 and the corresponding face of the facet joint. As will be appreciated by those skilled in the art, any portion of either (or both) opposed surfaces 18, 20 can include any amount of textured area 40 and remain within the spirit and scope of the present invention. Further, as will also be appreciated, any type of texturing capable of increasing friction between the bone-contacting surface 18 of the wedge body 12 and the corresponding face of the facet joint is within the spirit and scope of the present invention. Additionally, as will also be appreciated, a surface coating can be applied to temporarily decrease or eliminate the friction caused by the textured area 40 during insertion.

Figure 5:
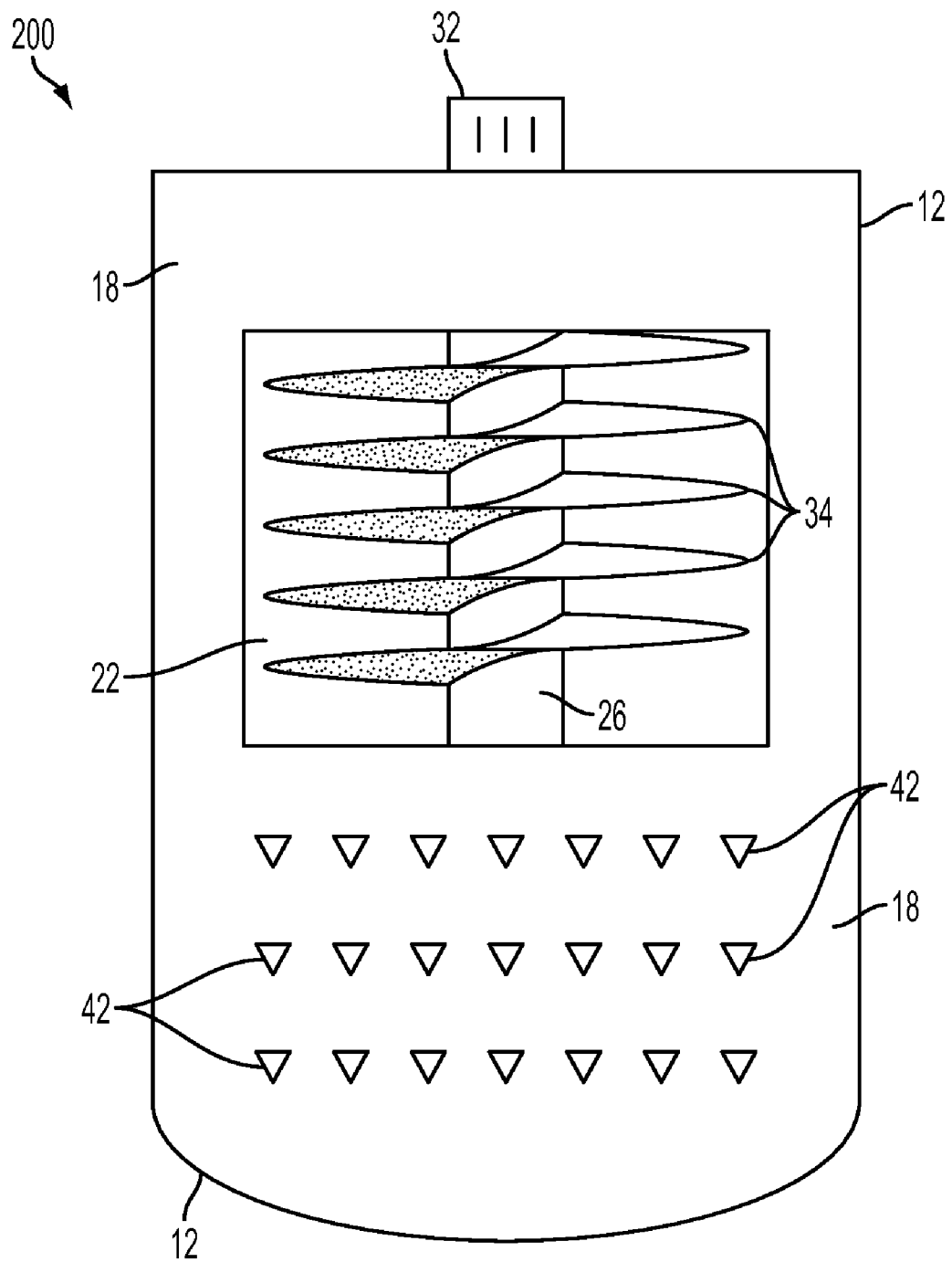
FIG. 5 is a top view of another embodiment of a spinal implant.

By way of example, any number or type of protrusions can be included on either bone-contacting surface 18, 20 such that the protrusions protrude from the surface 18, 20 to secure the implant to the facet joint and/or to increase the friction between the surface 18, 20 and corresponding face of the facet joint. FIG. 5 thus illustrates an embodiment of the implant 200 that includes a plurality of protrusions 42 (e.g., barbs) disposed on the top bone-facing surface 18 of the wedge body 12. FIG. 3B shows a side view of the protrusions 42 disposed on the top bone-contacting surface 18. As shown, the barbs 42 are configured and disposed on the surface 18 so as to enhance the stability of the implant by increasing the friction between at least the top surface 18 of the wedge body 12 and the corresponding face of the facet joint. Likewise, any other type (or combination) of elements (e.g., spikes, keels, blades, barbs, etc.) protruding out from at least one of the bone-contacting surfaces 18, 20 in order to enhance friction and/or surface area contact with a corresponding face of the facet joint is within the spirit and scope of the present invention. One skilled in the art will appreciate that such protrusions can optionally be bone penetrating.

Figure 6:
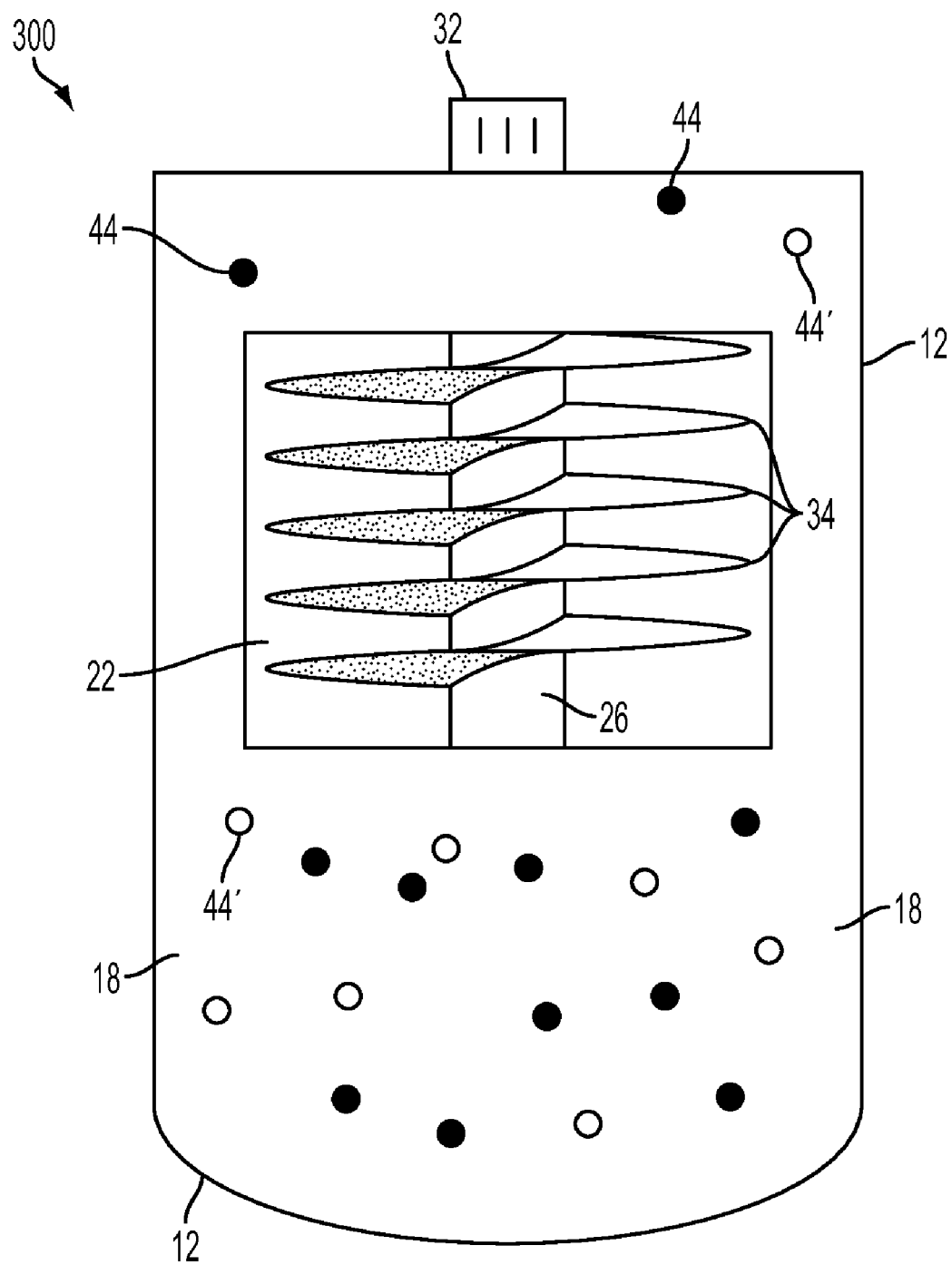
FIG. 6 is a top view of yet another alternative embodiment of a spinal implant.

Another example of a surface texture is shown in FIG. 6 in which at least one of the opposed bone-contacting surfaces 18, 20 of the wedge body 12 includes a plurality of pores 44, 44'. More specifically, the surfaces 18, 20 can include at least one pore 44 extending partially into the wedge body 12. Also, the wedge body 12 can include at least one pore 44' extending from the top bone-contacting surface 18 to the bottom bone-contacting surface 20. Pores 44, 44' can allow bone in-growth into and/or through the wedge body 12 thereby allowing the wedge body to be further solidified within the facet joint. As will be appreciated by those skilled in the art, any number, size, and/or orientation of these pores 44, 44' are within the spirit and scope of the present invention.

The wedge body 12 can be formed of various types of biocompatible and bioimplantable materials. For example, the wedge body 12 can include any type of biocompatible polymer, resorbable polymer, osseointegrating polymer, bioceramic, metal, metal alloy, or any such combination. Further, the wedge body 12 can include any type of material capable of taking the shape of the implant seating area within the facet joint (e.g., a flexible material) thereby allowing for a better fit of the implant 10 within a wide range of facet joints. In another embodiment, the wedge body 12 can include a material capable of substantially solidifying once placed within the facet joint. These formable materials, such as a curable resin or calcium phosphate cement in a flexible envelope, allow for the implant to adapt to the configuration of the facet joint prior to taking a final form. Once again, use of such a formable material allows for the implant 10 to be utilized with a wide range of facet joints of various configurations, while also enhancing contact between the implant 10 and the opposing faces of the facet joint.

Looking in more detail at the flexible envelope embodiment, the envelope can be formed of a wide range of materials. Additionally, the envelope can be porous or non-porous. For example, the envelope can include a biodegradable textile, a polylactic acid ("PLA")/polyglycolic acid ("PGA") blend, polyethylene terephthalate ("PET"), porous polytetrafluoroethylene ("PTFE"), bio-engineered silk, etc. Likewise, various filler materials can be disposed within the envelope. For example, these materials can include minced biological tissue (e.g., bone graft), demineralized bone matrix, collagen, tricalcium phosphate particles, bioglass particles, calcium phosphate cements, dental resins, polymethyl methacrylate ("PMMA"), silicone rubber, radio-opaque particles (e.g., barium sulfate), etc. Those skilled in the art will appreciate that various other materials capable of forming or being disposed within the flexible envelope are within the spirit and scope of the present invention.

Embodiments of the wedge body 12 can also include various fusion-promoting bioactive materials. For example, the entire wedge body 12 or a portion of the wedge body 12 can include such a fusion-promoting material. Additionally, the wedge body 12 can include a coating of the fusion-promoting material. Also, a core of the wedge body 12 can include the fusion-promoting material such that the fusion-promoting material can escape from the wedge body 12 once the wedge body 12 is properly placed within a desired facet joint. As will be appreciated by those skilled in the art, any such fusion-promoting bioactive material is within the spirit and scope of the present invention. However, examples of such fusion-promoting bioactive materials can include allograft bone, xenograft bone, bone morphogenic protein (BMP), tricalcium phosphate (TCP), hydroxyapatite (HA), biocoral, bioglass, bioceramic, and polymer composites.

As mentioned above, the various embodiments of the implant 10 include at least one drive screw 24 disposed within the wedge body. As shown in FIGS. 1A-3B, the drive screw 24 includes a shaft 26 having a proximal 28 and distal end 30. Further, the screw 24 includes at least one thread 34 running along a portion of the shaft 26. Additionally, a screw head 32 can extend from the proximal end 28 of the screw 24 such that the screw head 32 is surgically accessible to the trailing end 14 of the wedge body 12 (for example, recessed within an internal drive feature, or prominent from the trailing end 14 of the wedge body 12 with internal and/or external drive features). The screw head 32 can be capable of receiving a driver instrument (such as a screw driver, not shown) and thereby turning the drive screw 24 and advancing the implant 10.

As illustrated in FIGS. 1A-3A, the screw 24 can be disposed within the wedge body 12 such that a longitudinal axis of the screw 24 is substantially co-linear with a longitudinal axis of the wedge body 12. Such a configuration can allow the threads 34 of the threaded portion of the screw 24 to protrude from the top and bottom openings 22, 22' and beyond the opposed bone-contacting surfaces 18, 20 of the wedge body 12. As indicated by dashed lines in FIG. 1A, the distal end 30 of the screw 24 can extend from the inner cavity of the wedge body 12 into a corresponding channel (not shown) of the wedge body 12 so as to secure the distal end of the screw 24 within the wedge body 12. Likewise, a length 28a of the proximal end 28 can extend through a similar, corresponding channel (not shown) of the wedge body 12 which allows the screw 24 to extend from the inner cavity of the wedge body 12, through the cut-out, and terminate in a screw head 32 positioned, adjacent to the trailing, proximal end 14 of the wedge body 12. The screw 24 can be secured within or the screw 24 can key into the wedge body 12 by a variety of techniques. For example, the wedge body can be treated with heat or chemically treated to adhere the screw 24 to the wedge body 12. Furthermore, as will be appreciated by those skilled in the art, various surface treatments and/or adhesives (e.g., epoxy) can be applied to the screw 24 to further secure the screw to the wedge body. Those skilled in the art will appreciate will further appreciate that various other methods and materials can be employed to engage the screw to the wedge body; all such alternatives are within the spirit and scope of the present invention.

The screw 24 can likewise be formed from a wide range of materials. For example, the screw can include any biocompatible metal, metal alloy, polymer, or combination of such materials. In an exemplary embodiment, the screw is formed from titanium or a titanium alloy. Furthermore, like the wedge body 12, the screw 24 can include a fusion-promoting bioactive material.

Although the implant is described and illustrated to have a single screw, one skilled in the art will appreciate that the implant can include two or more screws. In one example, the implant can include two screws disposed adjacent to each other such that each screw 24 is positioned on either side of the longitudinal axis of the wedge body 12. As will be appreciated by those skilled in the art, any number of similarly positioned screws 24 are within the spirit and scope of the present invention.

The threaded portion(s) of the screw 24 can include threads of various sizes and dimensions. In general, the threaded portion(s) 34, 34' can be configured to facilitate delivery to the facet joint as well as participate in distraction of the opposing faces. FIG. 3A illustrates an exemplary embodiment of a major ($D_{Max}$) and minor ($D_{Min}$) diameter of the thread 34 relative to the height of the wedge body 12. As shown, the major diameter ($D_{Max}$) of the thread 34 can be configured to be greater than the maximum height ($H_1$) of the wedge body 12 thereby allowing the thread 34 to protrude from the openings 22, 22' of the top 18 and bottom bone-contacting surfaces 20. Further, the minor diameter ($D_{Min}$) of the thread 34 can be adapted to be equal to or less than (as shown) the minimum height of the wedge body 12. In an alternative embodiment, the minor diameter can be greater than the minimum height of the wedge body. In an exemplary embodiment, the screw thread 34 major diameters ($D_{Max}$) can vary from about 4 mm to about 12 mm, and screw minor diameters ($D_{Min}$) can vary from about 1 mm to about 8 mm. Those skilled in the art will appreciate that various other dimensions are within the spirit and scope of the present invention.

As shown in FIG. 3A, the thread 34 can include a substantially constant major diameter ($D_{Max}$) as well as a substantially constant distance between adjacent thread peaks. In an alternative embodiment, as shown in FIG. 3B, the major diameter of the thread 35 can continuously increase along the length of the screw 24 as the height of the wedge body increases. In other embodiments, the height of the thread can increase variably. As will be appreciated by those skilled in the art, any such profile of the major and/or minor diameter of the thread is within the spirit and scope of the present invention.

The size and positioning of the treads 34 can vary and these properties can be configured to provide various functions. For example, the thread 34 can be configured to engage opposing faces of a facet joint, and advance the implant 10 into facet joint by as a rotational force is delivered to the screw 24 via the screw head 32 (or similar mechanism). Furthermore, the threads 34 can be configured to engage opposing faces of the facet joint so as to stabilize the joint by providing a desired degree of distraction to the joint. In such an embodiment, the screw can be adapted to distract the opposing faces to relieve stenosis. Additionally, the threads 34 can be configured to engage opposing facets of the facet joint and act as stand-offs thereby preventing the facet faces from contacting the wedge surface 18, 20 directly. In such an embodiment, the wedge body can act as a final stop between facet faces. The above-discussion identifies various aspects of the spinal implant disclosed herein. Those skilled in the art will appreciate that various modifications can be made to any of these embodiments and the modified implant will remain within the spirit and scope of the present invention. Additionally, those skilled in the art will appreciate that aspects from each of the various embodiments can be combined in a single implant and remain within the spirit and scope of the present invention.

In another aspect, a method is provided for placing a spinal implant within a facet joint in an intra-facet orientation to provide fixation and/or stabilization of the facet joint. As will be described, the various embodiments of the method provide enhanced safety, efficiency, and versatility relative to prior art methods.

Figure 7:
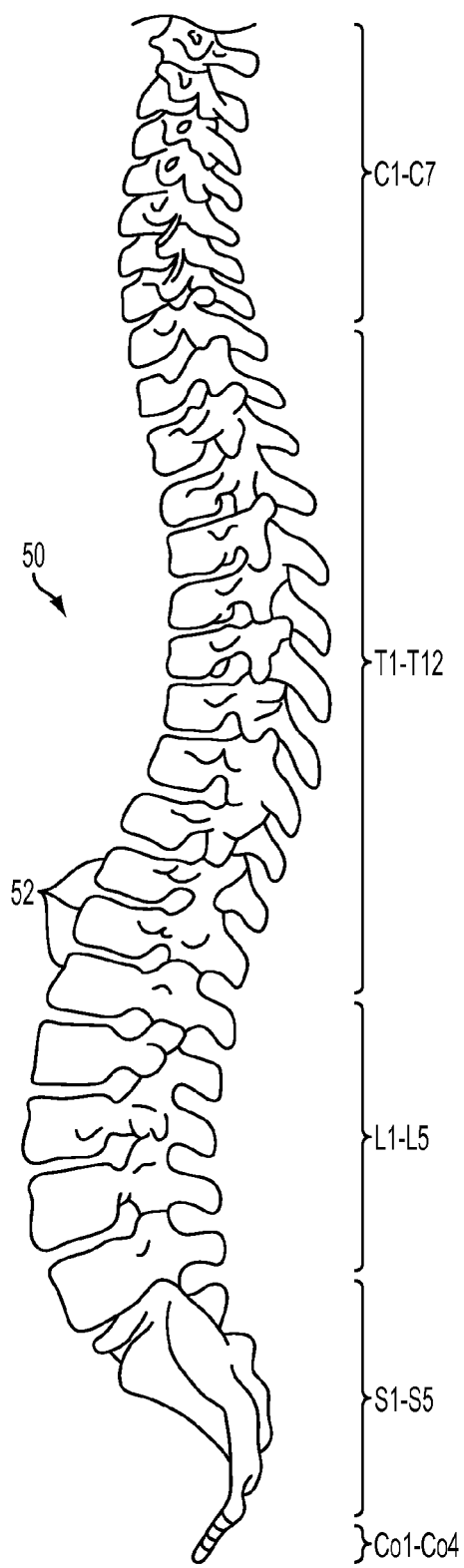
FIG. 7 is a representation of a human spinal column.

Before describing such intra-facet methods for stabilizing the facet joint, an overview of facet joint anatomy and prior art stabilization methods is provided. As FIG. 7 shows, the human spinal column 50 is comprised of a series of thirty-three stacked vertebrae 52 divided into five regions. The cervical region includes seven vertebrae 52, known as C1-C7. The thoracic region includes twelve vertebrae 52, known as T1-T12. The lumbar region contains five vertebrae 52, known as L1-L5. The sacral region is comprised of five vertebrae 52, known as S1-S5. The coccygeal region contains four vertebrae 52, known as Co1-Co4.

Figure 8:
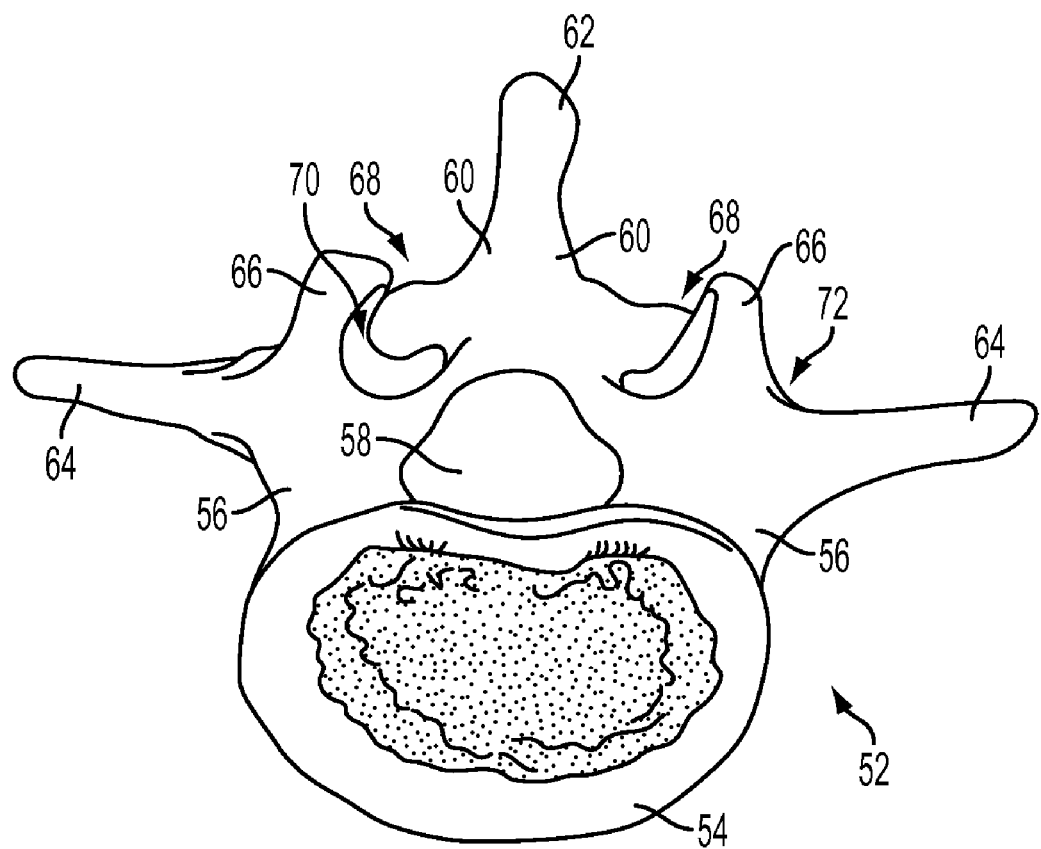
FIG. 8 is a representation of a lumbar vertebrae.

FIG. 8 shows a normal human lumbar vertebra 52. Although the lumbar vertebrae 52 vary somewhat according to location, they share many features common to most vertebrae 52. Each vertebra 52 includes a vertebral body 54. Two short bones, the pedicles 56, extend posteriorly from each side of the vertebral body 54 to form a vertebral arch 58. At the posterior end of each pedicle 56 the vertebral arch 58 flares out into broad plates of bone known as the laminae 60. The laminae 60 fuse with each other to form a spinous process 62, to which muscle and ligaments attach. A smooth transition from the pedicles 56 into the laminae 60 is interrupted by the formation of a series of processes.

Figure 9:
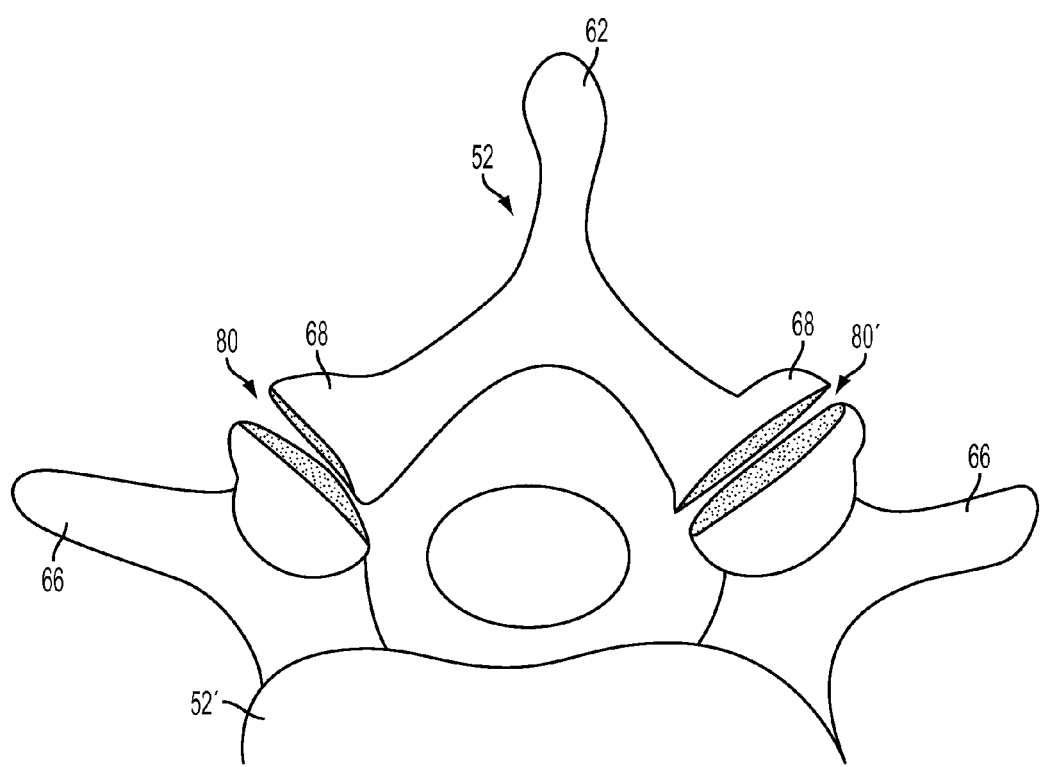
FIG. 9 is a representation of a first facet joint and a corresponding second facet joint formed as a result of a first vertebrae stacked on a second vertebrae.

Two transverse processes 64 thrust out laterally on each side from the junction of the pedicle 56 with the lamina 60. The transverse processes 64 serve as levers for the attachment of muscles to the vertebrae 52. Four articular processes, two superior 66 and two inferior 68, also rise from the junctions of the pedicles 56 and the laminae 60. The superior articular processes 66 are sharp oval plates of bone rising upward on each side from the union of the pedicle 56 with the lamina 60. The inferior processes 68 are oval plates of bone that jut downward on each side. The superior and inferior articular processes 66 and 68 each have a natural bony structure known as a facet. The superior articular facet 70 faces upward, while the inferior articular facet 72 faces downward. As shown in FIG. 9, when adjacent vertebrae 52, 52' are aligned (i.e., stacked), the facets interlock to form corresponding facet joints 80, 80' positioned at the same level of the spine.

Figure 10A:
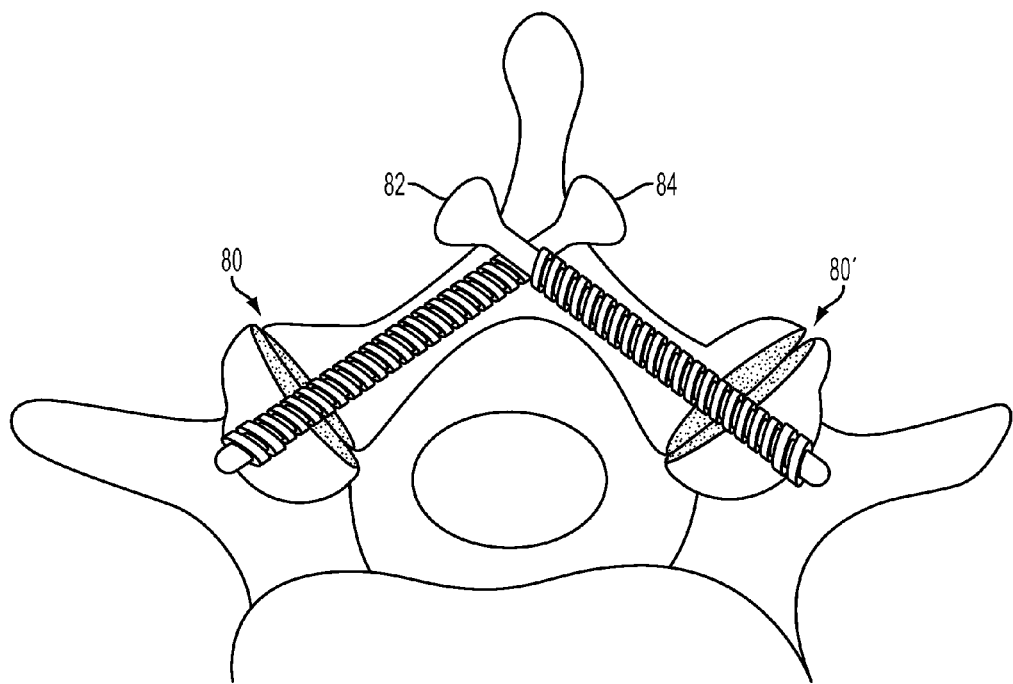
FIG. 10A is a representation of prior art trans-facet delivery of fixation screws.
Figure 10B:
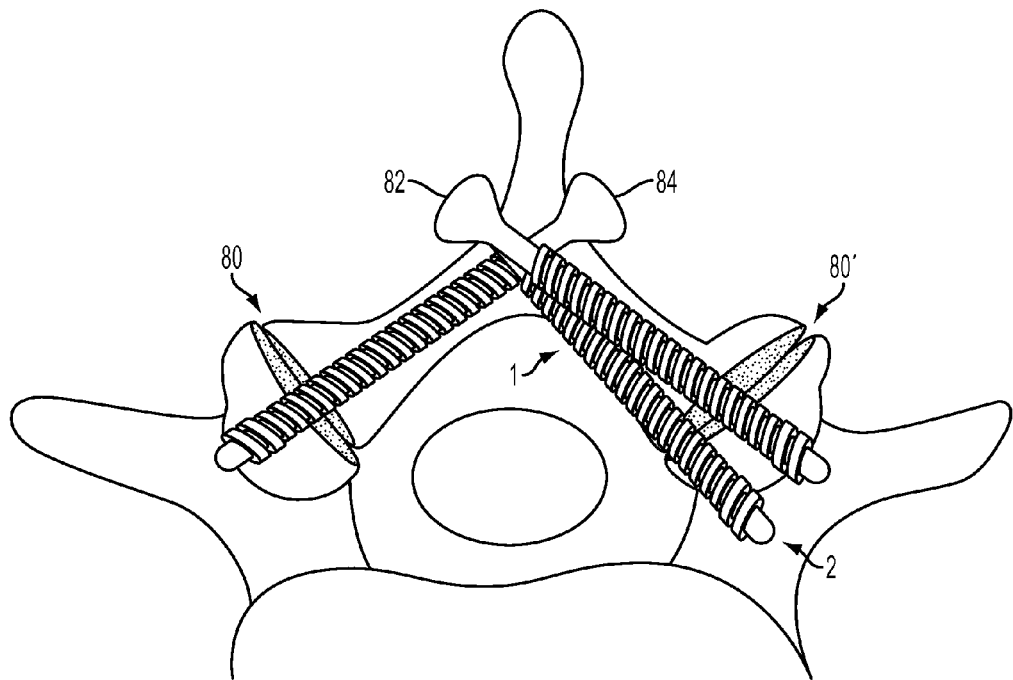
FIG. 10B is a representation of prior art trans-facet delivery of fixation screws wherein one of the trans-facet screws has impinged the spinal column.
Figure 10C:
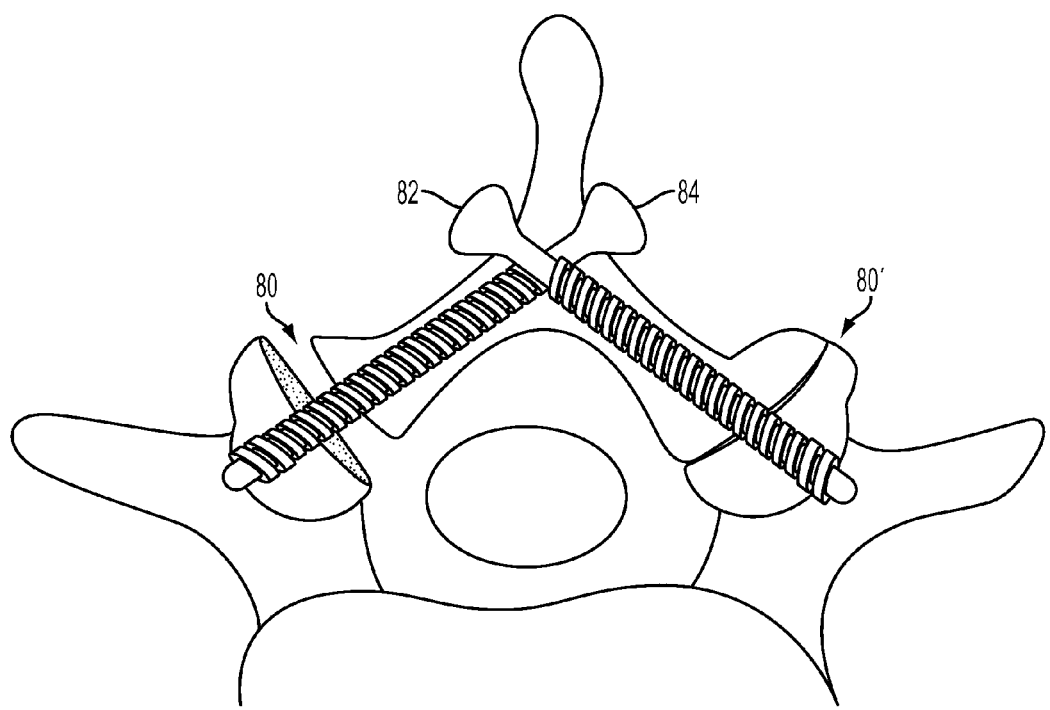
FIG. 10C is a representation of prior art trans-facet delivery of fixation screw wherein incorrect placement of the trans-lamina screws results in rotational distortion of the joint.

Looking in more detail at FIG. 9, the spinous process 62 and inferior articular processes 68 of the top vertebrae 52 are positioned adjacent to the superior articular processes 66 of the bottom vertebrae 52' and form facet joints 80, 80'. As shown in FIG. 10A, prior art trans-facet fixation procedure involves the insertion of trans-facet screws 82, 84 through bone and across the facet joints 80, 80'. However, such a procedure has been known to result in various problems. For example, FIG. 10B shows that a minor miscalculation in screw placement can result in a trans-facet screw 82 impinging upon the central spinal canal (as indicated by (1)) and/or impinging upon surrounding nerves (as indicated by (2)), thereby resulting in patient discomfort or injury. Additionally, trans-facet screw placement procedures can result in unwanted and/or unpredictable rotational distortion (or lateral offset) of the facet joint because of the difficulty of approximating the final position of the trans-facet screws 82, 84 in these procedures. As shown in FIG. 10C, trans-facet placement of the screws 82, 84 can result in significantly different gap sizes in corresponding facet joints 80, 80', thereby resulting in unwanted tension on the spine and ultimately injury to the patient.

Figure 11:
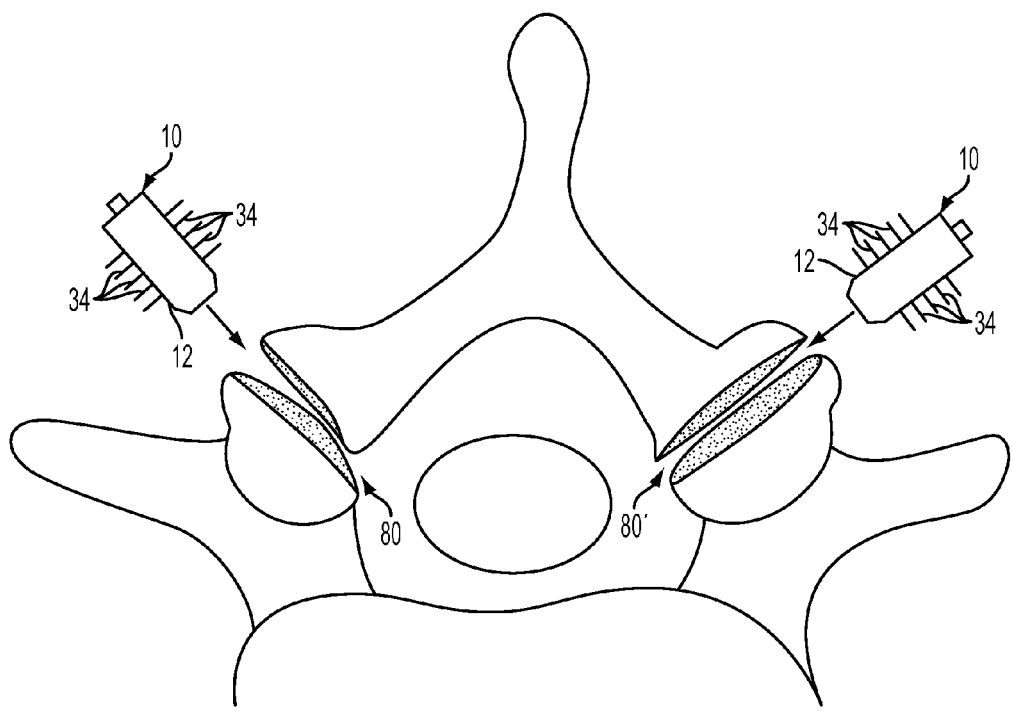
FIG. 11 schematically represents a first spinal implant being delivered to a first facet joint, and a second spinal implant being delivered to a second facet joint.

As shown in FIG. 11, an exemplary embodiment of the method can include delivering a first spinal implant 10 to a first facet joint 80 in an intra-facet orientation. Additionally, the method can include similarly delivering a second spinal implant 10 in a intra-facet configuration to a corresponding, second facet joint 80' positioned at the same height of the spinal column. The first and second implants can be substantially identical in size, or the implants can sized differently so as to allow proper positioning within facet joints of different sizes (or joints in need of different amounts of distraction.) As discussed above, the spinal implants 10 can be configured to engage a distal portion of the thread 34 of the implant 10 to opposing faces of the facet joint 80, and utilizing a rotational force applied to the threads 34 via the screw head 32 in order to advance the implant into the facet joint 80.

Figure 12:
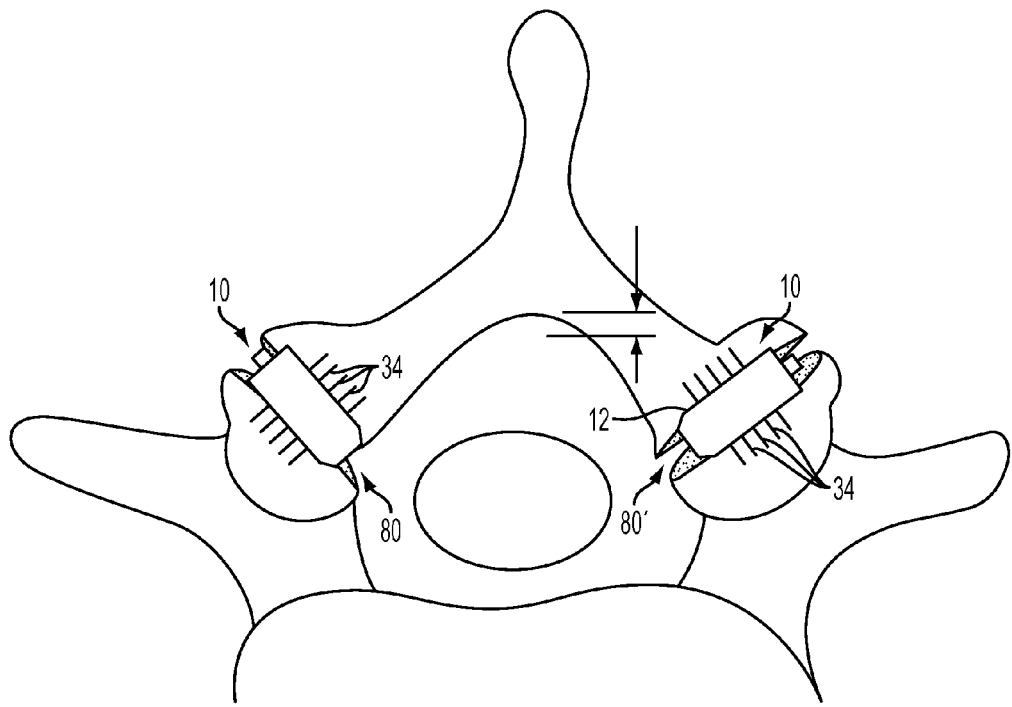
FIG. 12 is a schematic view representing the first spinal implant placed with the first facet joint, and the second spinal placed within the second facet joint.

FIG. 12 shows the first implant 10 placed within the first facet joint 80, and the second implant placed within the second facet joint 80'. In such a position, the threads 34 of the implant 10, as well as the wedge body 12, can secure the implant and provide stabilization of the facet joint 80, 80'. Further, as indicated by arrows in FIG. 12, the implant can provide a desired amount of distraction to the facet joint. In addition, as discussed above, a fusion-promoting bio-active material of the implant 10 (or screw 24) can be applied to the implant before or after installation to actively participate in promoting spinal fusion.

As an added benefit, the intra-facet spinal implant 10 and procedures disclosed herein are particularly well suited for minimally invasive surgery. That is, screws or similar devices can be placed in an intra-facet orientation using one or more small, percutaneous incisions, with or without the need for an access port. Such procedures, which are generally well known to those skilled in the art, tend to result in less operative trauma for the patient than a more invasive procedures. Minimally invasive procedures also tend to be less expensive, reduce hospitalization time, causes less pain and scarring, speed recovery, and reduce the incidence of post-surgical complications, such as adhesions.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for facet joint stabilization, comprising:
   utilizing a spinal implant having a wedge body with opposed bone-contacting surfaces, a distal, leading end and a proximal, trailing end, an opening formed in each of the bone contacting surfaces, such that each opening communicates with a cavity formed in at least a portion of an interior of the wedge body, and at least one screw disposed within the cavity of the wedge body such that proximal and distal threads formed on at least a portion of the screw protrude from the openings formed in the bone contacting surfaces, wherein the proximal thread is separated from the distal thread by an unthreaded portion of the screw;
   surgically delivering the spinal implant to a facet joint in an intra-facet configuration;
   engaging the distal thread to opposing faces of the facet joint; and
   rotating the screw to advance the wedge body into the facet joint.

2. The method of claim 1, wherein the screw has a major diameter greater than a maximum height of the wedge body from the distal, leading end to the proximal, trailing end.

3. The method of claim 2, wherein the screw has a minor diameter less than or substantially equal to a maximum height of the wedge body from the distal, leading end to the proximal, trailing end.

4. The method of claim 1, wherein the screw includes a head at a proximal end of the screw, the head being positioned adjacent to the trailing end of the wedge body.

5. The method of claim 1, wherein a height of the wedge body increases from the leading end to the proximal end.

6. The method of claim 1, wherein at least a portion of at least one of the bone-contacting surfaces is textured.

7. The method of claim 6, wherein the bone-contacting surface is a porous surface.

8. The method of claim 1, wherein two screws are disposed within the wedge body, the screws mounted on opposite sides of a longitudinal axis of the wedge body.

9. The method of claim 1, wherein the wedge body comprises a fusion-promoting bioactive material.

10. The spinal implant of claim 9, wherein the fusion-promoting bioactive material is selected from the group consisting of allograft, tricalcium phosphate, hydroxyl apatite, biocoral, bioglass, and polymer composites.

11. The method of claim 1, wherein the surgically delivering step is conducted in a minimally invasive surgical procedure.

12. The method of claim 1, wherein the distal thread extends distally beyond the distal end of the wedge body.

13. A method for facet joint stabilization, comprising:
    surgically delivering a wedge body to a facet joint in an intra-facet configuration, the wedge body having a screw being disposed therein such that a threaded portion of the screw protrudes from each of opposed bone-contacting surfaces of the wedge body and extends distally beyond a distal end of the wedge body;
    engaging the threaded portion to opposing faces of the facet joint; and
    rotating the screw to advance the wedge body distally into the facet joint.

14. The method of claim 13, further comprising adding a fusion-promoting bioactive material to the wedge body.

15. The method of claim 14, wherein the fusion-promoting bioactive material is selected from the group consisting of allograft, tricalcium phosphate, hydroxyl apatite, biocoral, bioglass, and polymer composites.

16. The method of claim 14, wherein the fusion-promoting bioactive material is allograft.

17. The method of claim 13, wherein the surgically delivering step is conducted in a minimally invasive surgical procedure.

18. A method for facet joint stabilization, comprising:
    surgically delivering a wedge body to a facet joint in an intra-facet orientation,
    engaging a distal thread of a screw to opposing faces of the facet joint to pull a distal portion of the wedge body between the opposing faces of the facet joint, wherein the distal thread extends distally beyond a distal end of the wedge body; and
    engaging a proximal thread of the screw to the opposing faces of the facet joint to pull a proximal portion of the wedge body between the faces of the facet joint.

19. The method of claim 18, wherein the wedge body is unthreaded.

20. The method of claim 18, wherein the screw includes an unthreaded region between the distal and proximal threads.

21. The method of claim 18, wherein the wedge body includes first and second openings, the proximal thread extending through the first opening and the distal thread extending through the second opening.

* * * * *